United States Patent

Masucci

[11] Patent Number: 5,833,991
[45] Date of Patent: Nov. 10, 1998

[54] GLYCINE-CONTAINING SEQUENCES CONFERRING INVISIBILITY TO THE IMMUNE SYSTEM

[75] Inventor: Maria G. Masucci, Sollentuna, Sweden

[73] Assignee: Cobra Therapeutics, Ltd., United Kingdom

[21] Appl. No.: 529,190

[22] Filed: Sep. 15, 1995

Related U.S. Application Data

[63] Continuation-in-part of Ser. No. 522,995, Sep. 1, 1995, abandoned.

[30] Foreign Application Priority Data

Apr. 10, 1995 [SE] Sweden .................................. 9501324

[51] Int. Cl.⁶ .......................... A61K 39/12; C07K 14/05; C07H 21/04
[52] U.S. Cl. ..................................... 424/185.1; 424/192.1; 424/230.1; 530/350; 536/23.4
[58] Field of Search ............................... 424/185.1, 192.1, 424/230.1; 530/350; 536/23.4

[56] References Cited

PUBLICATIONS

Hummel et al. Virology 148: 337 1986.
Bourdon et al PNAS 82: 1321, 1985.
Condit et al. Nature 323:178, 1986.
Levitskaya et al., *Nature* 375:685–688 (1995).

*Primary Examiner*—Thomas M. Cunningham
*Assistant Examiner*—Martha Lubet
*Attorney, Agent, or Firm*—Kathleen M. Williams; Banner & Witcoff, Ltd.

[57] ABSTRACT

The invention provides compositions and methods for preventing undesired immune responses in which a recombinant protein is prepared which includes a glycine-containing amino acid sequence, protein substantial invisibility to the immune system.

8 Claims, 5 Drawing Sheets

NH₂- Gly-Ala-Gly-Ala-Gly-Ala-Gly-Gly-Ala-Gly-Gly-Ala-Gly-Ala-
Gly-Gly-Ala-Gly-Ala-Gly-Gly-Ala-Gly-Gly-Ala-Gly-Ala-
Gly-Gly-Ala-Gly-Ala-Gly-Gly-Ala-Gly-Gly-Ala-Gly-Gly-
Gly-Ala-Gly-Ala-Gly-Gly-Ala-Gly-Gly-Ala-Gly-Gly-Gly-
Ala-Gly-Gly-Ala-Gly-Ala-Gly-Gly-Ala-Gly-Gly-Ala-Gly-Ala-
Gly-Ala-Gly-Gly-Ala-Gly-Gly-Ala-Gly-Gly-Ala-Gly-Gly-
Ala-Gly-Gly-Ala-Gly-Ala-Gly-Gly-Ala-Gly-Gly-Ala-Gly-
Ala-Gly-Ala-Gly-Gly-Ala-Gly-Ala-Gly-Gly-Ala-Gly-Gly-
Ala-Gly-Ala-Gly-Gly-Ala-Gly-Gly-Ala-Gly-Ala-Gly-Gly-
Gly-Ala-Gly-Gly-Ala-Gly-Gly-Ala-Gly-Ala-Gly-Ala-Gly-
Ala-Gly-Ala-Gly-Gly-Ala-Gly-Gly-Ala-Gly-Ala-Gly-Gly-
Ala-Gly-Gly-Ala-Gly-Ala-Gly-Gly-Ala-Gly-Gly-Ala-Gly-Ala-
Gly-Gly-Ala-Gly-Ala-Gly-Gly-Ala-Gly-Gly-Ala-Gly-Ala-
Gly-Gly-Ala-Gly-Ala-Gly-Gly-Ala-Gly-Gly-Ala-Gly-Ala-
Gly-Gly-Gly-Ala-Gly-Ala-Gly-Gly-Ala-Gly-Ala -COOH

FIG. 1

GLYCINE-CONTAINING SEQUENCES CONFERRING INVISIBILITY TO THE IMMUNE SYSTEM

This application is a continuation-in-part application of U.S. Ser. No. 08/522,995 filed September 1, 1995.

BACKGROUND OF THE INVENTION

The use of recombinant DNA technology for production of vaccines and transfer vectors for gene therapy has opened new possibilities for the prevention and cure of diseases. Actual gene therapy approaches are based on the introduction in the somatic cells of the host of gene sequences from the same or other species. Amongst the genes of interest are those coding for active substances such as enzymes, hormones or cytokines, immunogenic protein from viruses, bacteria or parasites or intracellular control proteins that regulate gene expression and cell growth.

Several methods have been developed to optimize the transfer of exogenous genes to somatic cells. Some methods employ recombinant vectors that are obtained by genetic manipulation of native viruses such as vaccinia viruses, adenoviruses or retroviruses. The viruses are rendered non pathogenic by modification of endogenous genes and parts of the virus genetic material (DNA or RNA) is exchanged for a gene of interest. Alternatively, isolated DNA fragments coding for the gene of interest are introduced in somatic cells via inert carriers, such as liposome vectors, or via so called "gene gun" methods whereby DNA/RNA coated carriers, e.g. gold particles, are shot at high pressure into dermal cells.

One potential problem in gene therapy is that the host immune system may recognize as foreign therapeutic material that has been introduced into the host. For example, where a transfer vector carrying a gene encoding a therapeutic protein is used to introduce a gene into a mammal, a host immune response directed to structural or regulatory proteins of the transfer vector may be induced. Another potential problem is induction of an immune response to the foreign therapeutic protein.

Foreign proteins are processed in the target cells and presented at the cell surface in association with MHC class I or class II molecules. Cells expressing foreign proteins are recognized by the immune system and eliminated Strong memory responses are activated when the recombinant DNA or recombinant protein is readministered resulting in significant impairment of therapeutic efficacy. This problem can be obviated by the administration of immunosuppressive drugs, however such drugs are usually potent overall inhibitors of the immune system and thus have serious side effects, such as increased risk of opportunistic infections and virus induced malignancies. There is, therefore, substantial interest in developing methods for selectively inhibiting immune responses that will favor the long term persistence of cells expressing immunogenic proteins and eliminate the need for pharmacologically induced immunosuppression.

SUMMARY OF THE INVENTION

The invention is based on the discovery that a glycine-rich repeat sequence, when inserted into a protein which is normally antigenic, confers upon the recombinant protein the ability to evade the immune system. Thus, the invention allows for selective inhibition of immune responses in that cells bearing the recombinant protein are not eliminated by the immune system.

The invention features a recombinant glycine-containing amino acid sequence having the formula:

$$[(Gly_a)X(Gly_b)Y(Gly_c)Z]_n$$

(SEQ ID NO:49) wherein each $Gly_a$, $Gly_b$, $Gly_c$, independently, may be one, two, or three sequential glycine residues; each of X, Y and Z is, independently, a hydrophobic or polar amino acid without a ring structure and having a side-chain of less than 3 atoms, wherein each of X, Y and Z, respectively, need not be identical from n repeat to n repeat; and n may be from 1–66.

In preferred embodiments, each of X, Y and Z is, independently, selected from the group consisting of Ala, Ser, Val, Ile, Leu and Thr; more preferably, each of X, Y and Z is, independently, one of Ala and Ser; most preferably, each of X, Y and Z is, independently, Ala; more preferably, each of X and Y is not Met or Cys.

In other preferred embodiments, the glycine-containing sequence comprises (GlyGlyXGlyYGlyZ) (SEQ ID NO:50) and n=7 repeats; or (GlyGlyXGlyYGlyGlyZ) (SEQ ID. NO:57) in n=9 repeats where the remaining n repeats comprise $(Gly_a)X(GlY_b)Y(Gly_c)Z$ (SEQ ID NO:49) up to a total repeat number of 66, and preferably 28 total repeats; or the glycine-containing sequence is (GlyGlyXGlyYGlyGlyGlyZ) (SEQ ID NO:52) in n=7 repeats where the remaining n repeats comprise $(Gly_a)X(Gly_b)Y(Gly_c)Z$ (SEQ ID NO:49) up to a total repeat number of 66, and preferably 28 total repeats; or the glycine-containing sequence comprises (GlyGlyAlaGlyAlaGlyGlyAla) (SEQ ID NO:53) in n=9 repeats where the remaining n repeats comprise $(Gly_a)X(Gly_b)Y(Gly_c)Z$ (SEQ ID NO:49) up to a total repeat number of 66, and preferably 28 total repeats.

Most preferably, the glycine-containing sequence is (GlyGlyAlaGlyAlaGlyGlyGlyAla)(SEQ ID NO:54) in n=7 repeats where the remaining n repeats comprise $(Gly_a)X(Gly_b)Y(Gly_c)Z$ (SEQ ID NO:49) up to a total repeat number of 66, and preferably 28 total repeats; or the glycine-containing sequence is (GlyGlyXGlyYGlyGlyZ) (SEQ ID NO:51) in n=9 repeats and (GlyGlyXGlyYGlyGlyGlyZ) (SEQ ID NO:52) in n=7 repeats where the remaining n repeats comprise $(Gly_a)X(Gly_b)Y(Gly_c)Z$ (SEQ ID NO:49) up to a total repeat number of 66.

The glycine-containing sequence (GlyGlyAlaGlyAlaGlyGlyAla) (SEQ ID NO:53) in n=9 repeats and (GlyGlyAlaGlyAlaGlyGlyGlyAla) (SEQ ID NO:54) in n=7 repeats is also preferred, where the remaining n repeats comprise $(Gly_a)X(Gly_b)Y(Gly_c)Z$ up to a total repeat number of 66.

The most preferred embodiment of the glycine-containing sequence is wherein, the sequence consists essentially of the amino acid sequence. (SEQ ID NO: 1) presented in FIG. 1, which is the EBNA1 glycine-rich sequence.

The invention also features a recombinant protein containing the above-described glycine-containing amino acid sequence, the recombinant protein comprising a core protein and the glycine-containing sequence.

Although the glycine-containing sequence may be joined to either the carboxy or amino terminal end of the core antigen protein, or inserted anywhere within the antigenic protein to render that protein non-antigenic, it is preferred that the glycine-containing sequence is inserted within the core protein at a distance wherein either terminal residue of the glycine-containing sequence is at a distance of between about 1 and 300 residues from an epitope of the protein. Preferably, the core protein is antigenic and contains one or more epitopes. In the case of an antigenic protein containing multiple epitopes, it is believed that all epitopes of the antigenic protein will be rendered non-antigenic according to the invention. Preferably, the distance between the site of insertion in the core protein of the glycine-containing sequence and one amino acid of the core protein epitope is between about 1 and 200 residues, more preferably 10–100 residues, and most preferably between about 20 and 50 residues. As used herein, "epitope" refers to an antigenic stretch of about 8–20 amino acids within a protein that is immunologically recognized as foreign.

The invention also encompasses a recombinant nucleic acid encoding the glycine-containing sequence described above, recombinant nucleic acid encoding a recombinant protein having inserted therein or at a carboxyl or amino terminal end thereof the glycine-containing sequence, and bacterial or mammalian host cells containing such recombinant nucleic acids.

The invention also encompasses methods of testing for glycine-containing sequences which confer on a recombinant protein containing such a sequence the ability to evade the immune system, the method comprising the steps of incubating a host cell that expresses a recombinant protein of the invention containing a glycine-containing sequence with a cell of the immune system that is specific for an epitope that is common to said recombinant protein and a reference protein, under conditions which allow for immunological recognition of said epitope, wherein said epitope is known or determined to be immunogenic in said reference protein in that an immune system cell immunologically recognizes (i.e., is able to bind, lyse, or is itself stimulated by binding to) a host cell bearing the reference protein or said epitope thereof, and wherein the absence of immunological recognition is indicative of evasion of the immune system.

Preferably, said immunological recognition is MHC class I restricted lysis of said host cell bearing said reference protein or epitope thereof. Alternatively, said immunological recognition comprises the ability of a host cell bearing said reference protein or epitope thereof to induce production of a lymphokine, such as INF, TNF, or one or more interleukins.

The invention also encompasses methods of selectively evading an immune response in a mammal, preferably a human, comprising administering to a mammal a recombinant protein comprising the glycine-containing sequence described herein, which protein is immunogenic in the absence of the glycine-containing sequence and non-immunogenic in the presence of such sequence.

As used herein, a protein or epitope of a protein is "immunogenic" or "antigenic" when it is recognized by immunocompetent cells (i.e., cells of the immune system). Recognition of immunocompetent cells is indicated when the protein or epitope triggers activation of such cells, as measured in terms of proliferation and/or induction of effector functions, e.g., as measured by production of lymphokines, cytokines, and/or killing of cells expressing the protein or epitope. Therefore, protein or epitope is "non-immunogenic" (non-antigenic) when is not recognized by immunocompetent cells, as explained above. "Selectively evading an immune response" refers to the ability to inhibit an MHC class I restricted CTL response to a protein of interest, and thus can be determined, at least initially, via in vitro CTL assays.

The invention also encompasses methods of selectively evading an immune response in a mammal, comprising administering to a mammal nucleic acid encoding a recombinant protein comprising the glycine-containing sequence described herein, which protein is immunogenic in the absence of the glycine-containing sequence and non-immunogenic in the presence of such sequence.

Further features and advantages of the invention will become more fully apparent in the following description of the embodiments and drawings thereof and from the appended claims.

BRIEF DESCRIPTION OF THE DRAWING

Before describing the invention in detail, the drawings will be described.

FIG. 1 provides the amino acid sequence (SEQ ID NO:1) of the internal gly-ala repeat of the EBNA1 protein from the B95.8 EBV strain.

DETAILED DESCRIPTION

Figure 2:
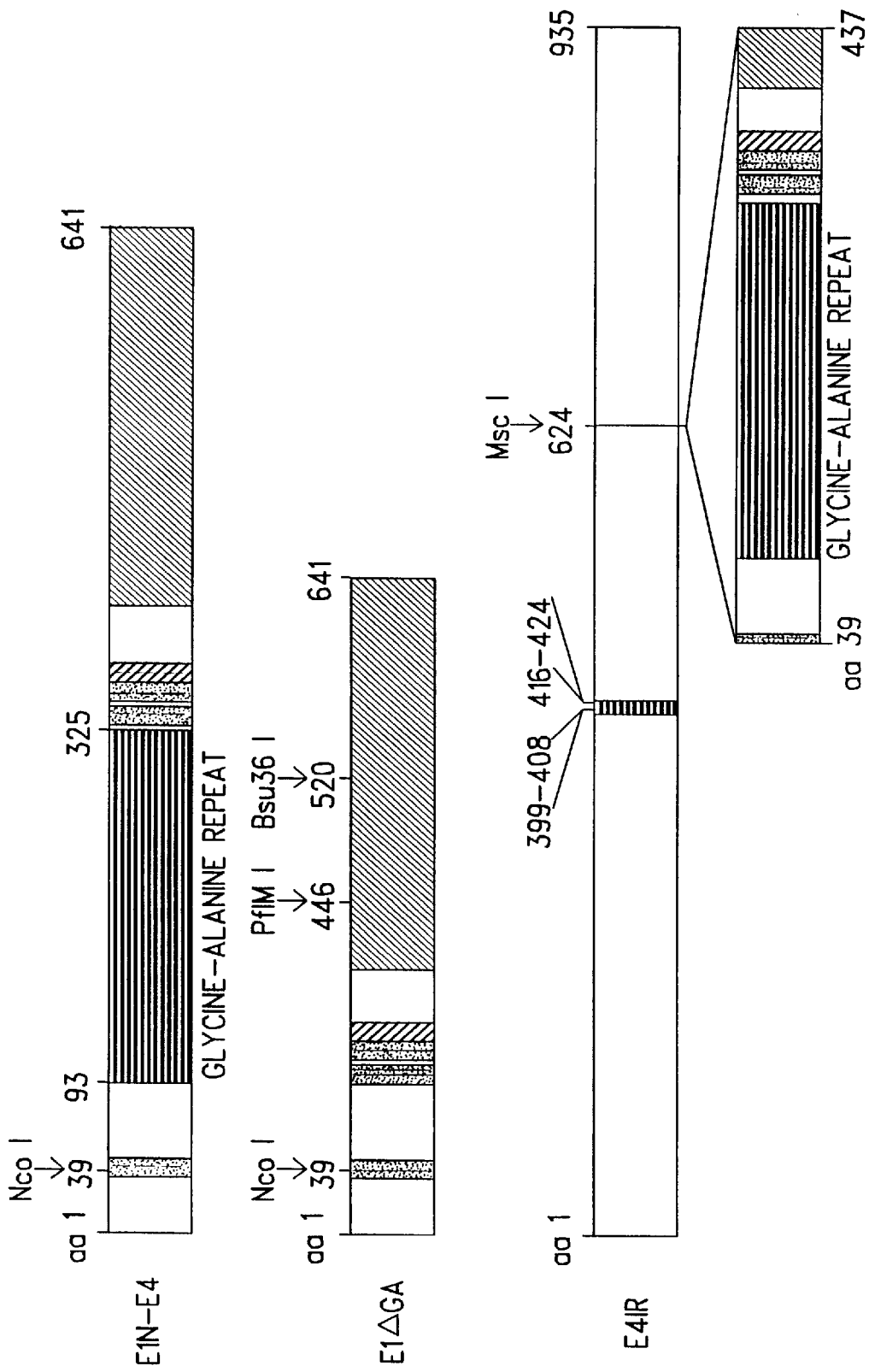
FIG. 2 is a schematic outline of the full length EBNA1 chimera, gly-ala deleted EBNA1 chimeras and gly-ala containing EBNA4 chimera. The restriction site and position of insertion of the EBNA4 416–424 epitope and EBNA1 internal repeat region (IR) are indicated by vertical arrows pointing to the amino acid number in the B95.8 sequence. The known EBNA1 protein domains are indicated as follows: gly-ala repeats (black box); gly-arg (grey box); nuclear localization signal (hatched box); DNA binding and dimerization domains (striped box).

The invention is based on the discovery that a glycine-rich sequence, when inserted into a protein which is normally antigenic, confers upon the recombinant protein the ability to evade the immune system. Without being bound to any one theory, it is proposed that the recombinant protein containing the glycine-rich sequence is able to avoid antigen presentation and/or processing.

The invention provides compositions and methods for preventing undesired immune responses in which a recombinant protein is prepared which includes a glycine-containing amino acid sequence, the glycine-containing sequence conferring upon the recombinant protein substantial invisibility to the immune system.

Example I describes how to make a recombinant glycine-containing sequence of the invention. Example II describes how to insert such sequences into a core protein to form a recombinant protein of the invention. Example III describes how to test a recombinant protein containing a glycine-containing sequence of the invention for effectiveness in evading the immune response. Example IV describes the EBNA1 glycine-containing repeat sequence. Example V describes experiments in which a foreign epitope is inserted into either the EBNA1 protein or an ENBA1 deletion mutant lacking the glycine-containing repeat sequence, and demonstrates that only the non-deleted EBNA1 protein confers non-immunogenicity on the inserted foreign epitope. Example VI describes experiments in which EBNA1 was overexpressed in the presence of another antigenic protein, and demonstrates that EBNA1 does not confer trans-acting inhibition of immunogenicity of the antigenic protein. Example VII describes experiments in which the EBNA1 glycine-containing sequence was inserted into a foreign protein, rendering the recombinant foreign protein non-immunogenic.

The invention is illustrated by the following nonlimiting examples wherein the following materials and methods are employed. The entire disclosure of each of the literature references cited hereinafter are incorporated by reference herein.

EXAMPLE I

Glycine-Containing Sequences Useful According To The Invention

Recombinant glycine-containing sequences of the invention having the following properties. Functionally, such sequences, when present in-cis in a recombinant protein, are able to render the protein non-immunogenic. Immunogenicity, or lack thereof, may be assessed by the capacity of the inserted sequence to inhibit specific cytotoxic responses measured in vitro and/or in vivo immunization tests as described below.

Recombinant glycine-containing sequences are defined structurally according to the generic formula, and preferred embodiments thereof, described herein. In addition to the generic formula, sequences of the invention are characterized in that they contain a repetitive stretch of glycines interspersed by single hydrophobic and/or polar amino acids. The presence of intercalating amino acids is likely to be required to prevent glycine from forming secondary structures.

Intercalating amino acids are likely to be small hydrophobic and/or polar, e.g., alanine, which has a short side chain consisting of a single —$CH_3$ group; serine, which also contains a single carbon atom side chain (—$CH_2OH$); valine, leucine, threonine and isoleucine, which are hydrophobic amino acids having side chains ranging from 2–4 carbon-containing groups. Without being bound to any one theory, it is proposed that a short side chain (i.e., 1–4 groups) inhibits formation of secondary structures in the target protein. Thus, Cys and Met are not likely to be suitable amino acids according to the invention because they contain a sulfhydryl group.

A comparison of the repetitive sequence in the EBNA1 protein of the B95.8 EBV strain and the Papio EBNA1-like antigen reveals that the generic formula provided hereinabove is repeated 7 times in Papio EBNA1 and 28 times in B95.8 EBNA1. In Papio, the generic motif is a regular repeat of GlyGlySerGlyAlaGlyAla (SEQ ID NO:55). The EBV EBNA1 repeat is not a regular repeat in that the number of Gly residues preceding each Ala varies from 1–3. However, some combinations appear more frequently, i.e., ($Gly_2AlaGly_1AlaGly_2Ala$) (SEQ ID NO:53) in n=9 of a total of n=28 repeats; and/or ($Gly_2AlaGly_1AlaGly_3Ala$) in n=7 of a total of n=28 repeats.

It should be understood that "functional derivatives" of the glycine-containing sequence present in FIG. 1 (i.e., the EBV EBNA1 sequence) refers to any sequence which confers non-immunogenicity on the protein in which it is inserted, and therefore may encompass sequences of varying length and composition (i.e., longer or shorter or internally deleted sequences may be functional and are testable for function as described below), and varying amino acid composition (additional amino acids may be included or exchanged for parts the original gly-ala sequence) as long as immune system evasion is maintained.

It is preferred that the total number of residues of the glycine-containing sequence be divisible by the number of basic residues of the repeat: $(Gly_{1-3})X_1(Gly_{1-3})X_2(Gly_{1-3})Z$, that is by 5, 6, 7, 8, 9, 10, or 11, depending upon the number of glycine residues present in each repeat. The number of repeats (n) in a glycine-containing sequence may be from 1–28 repeats and the total number of residues of the glycine-containing amino acid sequence is between 6 and 314. More preferably, n is 2, wherein the total number of residues of said sequence is 12–24, inclusive, or n is 7, wherein the total number of residues is 42–84, inclusive. Preferably, the total number of residues of the sequence is between about 400–600, where n=41 repeats with 8 residues remaining, and where n=66 repeats and 4 residues remaining.

Where a glycine-containing sequence is needed according to the invention, for example, for insertion into an antigenic protein to render it non-antigenic, the B95.8 EBNA1 sequence presented in FIG. 1 may be provided as described herein.

Alternatively, where another glycine-containing sequence is selected according to the generic formula and guidance for such sequence selection provided herein, it may be made according to any cloning strategy known to one of skill in the art. Two alternative strategies are described below; i.e., by PCR amplification of a prototype sequence or by oligo-merization of a selected minimal motif. The advantage of this latter strategy is that it can easily be modified to give repetitive sequences where the intervening X or Y amino acid or the Glycine backbone can be mutated in different combinations.

1. PCR Amplification

Where a DNA fragment encoding a glycine-containing sequence is available, the fragment may be used for PCR amplification, as follows.

A 1122bp long XmaI fragment of the prototype B95.8 BamHIK region containing the Glycine repeat sequence (coordinates 108117–109239 as described in Baer et al., Nature 310:207–211, 1984) may be used as template for PCR amplification. PCR primers are chosen immediately upstream and downstream of the repeats. Artificial BamHI and EcoRI sites are included in the sequences of the 5' and 3' oligonucleotides respectively. Amplification under low stringency conditions and the repetitive nature of the template allows for multiple priming and generation of PCR products of variable size. For example, the primer pair 5'-AAGGATCCAAGTTGCATTGGATGCAA-3' and 5'-TGAATTCTCGACCCCGGCCTCCACTG-3' may be used in a PCR reaction as follows: 50 nM of each primer ad 10–20 ng of each template are mixed in a 50 µl reaction buffer containing 1 mM Tris-HCl pH7.5, 5mM KCl, 0.15–0.5 nM $MgCl_2$, 0.001% gelatin, 200 µM DNTP and 2 units Taq DNA polymerase. Amplification conditions include 30–35 cycles of denaturation at 95° C. for 1 min, annealing at 45–60° C. for 1 min, and elongation at 72° C. for 1 min.

The PCR products are cloned in the BamHI and EcoRI sites of the pGEX-T2 vector downstream of the glutathione S-transferase gene (GST). The fusion protein GST-GlyAla is expressed in bacteria using the tac promoter. Expression of fusion proteins containing the repeats inserted in-frame downstream of the GST gene is then screened by Western blotting of lysates from single transformed colonies using affinity purified human antibodies specific for the EBNA1 GlyAla repeat (Dillner et al., 1984, Proc. Nat. Aca. Sci. 81;4652). Screening is performed after induction of individual bacterial clones grown in microwell plates with 0.3 mM IPTG in 150 µl LB medium for 4 hr. 80 µl of bacterial cell suspension is mixed with an equal volume of SDS-PAGE loading buffer and dotted onto nitrocellulose filters using a dot-blot apparatus. The filters are processed according to standard Western blot procedures and developed by ECL (Amersham).

Colonies expressing the GST-GlyAla polypeptide are further characterized to determine the size and coding capacity of the insert by restriction endonuclease analysis and sequencing. Plasmids encoding fusion proteins that contain repetitive inserts of 50, 100, 150, 200, 250, 300 amino acids (pGEX-(E1GlyAla)n) are selected for isolation of GlyAla encoding cassettes as described below.

2. Oligomerization of a selected minimal motif.

A set of complementary oligonucleotides encoding a core glycine-containing motif are synthesized with 5' and 3' overhangs to allow for oligomerization This strategy offers the advantage of producing known sequences that can easily be modified to include alternative amino acids.

Examples of complementary oligonucleotides encoding the core motif GlyAlaGlyAlaGlyGlyAlaGly (DEQ ID NO:3) and modifications thereof are provided in Table 1. The expected coding capacity upon insertion in positive or negative orientation relative to the direction of transcription is presented in Table 2. After annealing to form a duplex, the oligonucleotides will contain 5' and 3' overhangs corresponding to the initial amino acid codon and the first base of the adjacent codon and the first base of the adjacent codon to allow the formation of head-to-tail multimers upon ligation. Annealing is performed in a 50 µl reaction containing 100 µM of each primer, 0.1M $MgCl_2$, 10 mM Tris-HCl pH7.4. The reaction mix is heated at 72° C. for 5 min and allowed to proceed at 65° C. for additional 40 min. Ligation is performed by adjusting the annealing mix to 50 mM Tris pH 7.4 10 mM $MgCl_2$, 10 mM DTT, 1 mM spermidine, 1 mM ATP, 100 ng/ml BSA and by adding 10 u of T4 DNA ligase. The reactions are run for 1, 3, 6, 9 and 12 hrs at 15° C. Filling-in of the 3' recessed ends is performed with 0.1 u of the Klenow fragment of DNA polymerase in 50 mM Tris-HCl pH7.5, 7mM $MgCl_2$, 1 mM DTT and 20 µM dNTPs for 20 min at room temperature. Linear multimeric molecules are blunt-end ligated into the SmaI site of the pGEX-T2 vector as shown in Table 3. Clones expressing the GST-repeat fusion protein are selected by reactivity with GlyAla specific antibodies, as described herein. For fusion proteins containing repeats for which specific antibodies are not available, selection is performed on the basis of size after purification from the bacteria lysates on GST-binding glutathione-coated sepharose beads. Expressing clones are selected for further characterization of the inserts.

Plasmids are digested with BamHI and EcoRI that cut immediately upstream and downstream of the SmaI site in the pGEX-T2 vector. The inserts are size fractionated in 3% agarose gels and visualized by UV irradiation after ethidium bromide staining, Alternatively, plasmids and insert fragments obtained after BamHI/EcoRI digestion are end labelled with 1 unit Klenow fragment of DNA polymerase per µg plasmid in 25 µl reactions containing 50 mM Tris-HCl pH 7.5, 10 mM MgSO4, 1 mM DTT, 50µg/ml BSA Pentax fraction V, 2 nmoles dNTPs and 2pmoles $\alpha$-$^{32}$P-dCTP. Size fractionation is performed in 8% acrylamide gels. Plasmids containing inserts of sizes corresponding to the coding sequences of 2, 4, 8, 12 and 16 core repeats (48, 96, 192, 288, 384 bp, respectively) are further characterized by sequencing to confirm their coding potential and orientation of insertion.

A glycine-containing repeat sequence obtained according to the procedures described above is subcloned into a polylinker of an appropriate vector to generate subcloning cassettes containing unique upstream and downstream restriction sites. For example, subcloning into the BamHI and EcoRI sites of the pBluescript-SK vector (Stratagene) will generate subcloning cassettes containing unique upstream sites: SacI, BstXI, NotI, XbaI, and SpeI, and unique downstream sites HindIII, ClaI, HincII, AccI, SalI, XhoI, ApaI, DraII and KpnI.

EXAMPLE II

Recombinant Proteins Of The Invention Containing Glycine-Containing Sequences And Chimeric Genes Encoding Such Proteins Recombinant proteins of the invention which contain a glycine-containing sequences are made as follows.

1. Construction of chimeric genes encoding proteins containing Glycine repeat sequence.

A DNA cassette encoding a Gly-containing sequence is inserted into a selected site within a gene encoding a protein which is believed or known to be immunogenic in its natural form.

DNA encoding a candidate glycine-containing sequence is inserted into a gene encoding a protein of interest at a selected distance from a known epitope using conventional cloning procedures. It is preferred that the gly-containing sequence be inserted downstream (i.e., carboxy terminal to) of a selected epitope (i.e. an epitope to be rendered nonimmunogenic), e.g., at least 5 amino acids carboxy terminal to the epitope, more preferably at least 10–20 amino acids, at least 50 amino acids, 100 amino acids, or even at least 200 amino acids carboxy terminal to the epitope. Of course, the gly-containing sequence may be positioned at the carboxy terminus of the protein via an in-frame fusion.

By way of example, the cloning strategy for insertion of DNA encoding the glycine sequence (generically referred to as ("GlyX)n") into the influenza matrix protein is described in detail below.

Three unique restriction sites, RsaI, BamHI and StuI, are used for insertion of a (GlyX)n-encoding DNA cassette into the cDNA encoding the influenza matrix protein I from strain A/Puerto Rico/8/34 (matrix) (Winter et al., Nucl. Acids Res. 8:1965, 1980). In addition, the cassette encoding the Gly-containing sequence is inserted at the 3' end of the gene, immediately downstream of the matrix coding sequence. An immunodominant HLA A2 restricted CTL-specific epitope, referred to as GIL, has been identified in amino acid residues 58–66 (GILGFVFTL) (SEQ ID NO:43) of this 252 amino acid long protein (Bednerck et al., J. Immunol. 147:4047, 1991). The RsaI site is located at bp 28 relative to the initiating ATG codon, 47 amino acid residues upstream of the GIL epitope. The BamHI site is located at bp 264, 22 amino acids downstream of the GIL epitope and the StuI site is located at bp 713, 172 residues downstream of the epitope near the COOH terminus. The matrix cDNA is excised by EcoR1 digestion of pGS62 (Smith et al., Virol, 160:336, 1987) and recloned into the EcoR1 site of pGEM-9zf(-) (Promega) to create pGEM-matrix. GEM-matrix contains the matrix protein driven by the SP6 and T7 promoters for in vitro transcription/translation.

Construction of a chimeric gene containing a (GlyX)n-encoding cassette inserted into each of four different positions within the selected protein is described below. In each cloning example, care is taken to obtain cassette insertion in-frame within the coding sequence of the given protein, It will be understood by those of skill in the art that the examples presented below are representative cloning strategies for in-frame cassette insertion; modifications will be made as needed for a candidate (GlyX)n DNA cassette and a gene encoding a selected protein.

A DNA cassette encoding a Gly-containing sequence is subcloned into the RsaI site of the gene encoding the influenza matrix protein, as presented in Table 4 and as follows. pGEM-matrix plasmid is partially digested with RsaI. pGEM-9zf(-) contains a unique RsaI site located within the amp$^R$ gene. Recombinants containing the cassette inserted into this site will be selected against in this cloning procedure due to loss of amp resistance. A DNA fragment containing the (GlyX)n cassette is isolated via BamHI digestion. In the pGEX-T2(GlyX)n plasmid, the BamHI 3' recessed ends are then partially filled-in with A and G nucleotides. The DNA is then digested with EcoRI and the 5' protruding ends are removed by Mung bean exonuclease treatment. The modified fragment is blunt-end ligated into the RsaI site of the matrix protein coding region in the pGEM-matrix plasmid. Insertion in positive orientation will yield a chimeric gene encoding amino acids 1–9 of influenza matrix protein followed by the sequence PhePro(GlyX)nAsp (SEQ ID NO:74) and amino acids 11–252 of influenza matrix protein.

Subcloning of the (GlyX)n DNA cassette into the BamHI site of the gene encoding the matrix protein is presented in Table 5, and includes the following steps. The pGEM-matrix plasmid is digested with BamHI followed by Klenow of the 3' recessed ends. The (GlyX)n-encoding fragment is isolated from pGEX-2T(GlyX)n by BamHI/EcoRI digestion followed by partial filling of 3' recessed ends using A and G nucleotides, and Mung bean exonuclease treatment of the remaining 5' protruding ends. The (GlyX)n DNA fragment is blunt-end ligated into the filled-in BamHI ends of the pGEM-matrix plasmid. Insertion in positive orientation produces a chimeric gene encoding amino acids 1–88 of influenza matrix protein followed by the sequence LeuPro(GlyX)nGlu (SEQ ID NO:75) and amino acids 89–252 of influenza matrix protein.

Subcloning of the (GlyX)n DNA cassette into the StuI site of the gene encoding matrix protein is presented in Table 6 and includes the following steps. The pGEM-matrix plasmid is digested with StuI. The Gly-encoding cassette is isolated by BamHI digestion of the pGEX-2T-GlyX plasmid followed by partial filling in using A and G nucleotides. The plasmid is then digested with EcoRI and the 5' protruding ends are removed by Mung bean exonuclease treatment. The (GlyX)n fragment is blunt-end ligated into the StuI site of the pGEM-matrix plasmid. Insertion in positive orientation produces a chimeric gene encoding amino acids 1–238 of influenza matrix protein followed by the sequence VAlPro (GlyX)$_n$ (SEQ ID NO:76) and amino acids 239–252 of the matrix protein.

A fusion protein with a carboxyl terminal (GlyX)n sequence may also be made according to the invention. Subcloning of a DNA cassette encoding a (GlyX)n sequence into the 3' end of the influenza matrix protein gene is presented in Table 7 and includes the following steps. DNA encoding matrix protein is prepared by PCR amplification using the following respective 5' and 3' primers: 5'ATAAAGCTTATGAGTCTTCTAACCGAGGTC3' (SEQ ID NO:65) and 5'CGAGGATCCACTTGAACCGTTGCATCTGC3'(SEQ ID NO:66). The 5' primer contains an artificial HindIII site upstream of the first ATG and the 3' primer contains a BamHI site downstream of the codon for the last residue of the matrix protein.

The (GlyX)n DNA cassette is isolated by digestion of pGEX (GlyX)n with EcoRI, removal of 5' protruding ends with Mung bean nuclease, and digestion with BamHI. The plasmid into which the matrix protein coding sequence and the (GlyX)n cassette are inserted is pGEM-9zf digested with XbaI, treated with Mung bean nuclease, and further digested with HindIII.

The three thus-prepared DNAs, i.e., matrix-encoding DNA, (GlyX)n-encoding DNA, and the pGEM vector, are ligated in a single reaction involving site-directed ligation of matching HindIII ends, BamHI ends, or blunt-ends. The resulting plasmid, pGEM-matrix-(GlyX)n-COOH encodes a 242 amino acid matrix protein fused in-frame via its carboxyl terminal residue to the (GlyX)n sequence. Where the amino acid sequences are joined, two new residues (Trp and Ile) are created by the BamHI ligation. A UAG stop codon is present in-frame downstream of the fusion protein.

The correct orientation and reading frame alignment of the (GlyX)n-encoding insert is determined by DNA sequencing. Expression of the chimeric protein will be determined by western blots of in vitro translated material using antibodies specific for the influenza matrix protein (Smith et al., Virol., 160:336, 1987) and affinity purified anti-(GlyX)n antibodies, as described above. When desired, optimization of inhibition of immunogenicity of the protein of interest may be achieved by varying the size of the glycine-containing sequence or by varying the position of insertion of the gly-containing sequence relative to the immunogenic epitope.

2. Expression Of Chimeric Proteins Containing The Gly Repeat Sequence In Eukaryotic Cells.

Delivery systems are known in the art for introduction of foreign genes into eukaryotic cells. A chimeric gene according to the invention may be inserted into an appropriate delivery vehicle for delivery to a target cell. The delivery vehicle may be a viral vector or a non-viral vehicle. Where the chimeric gene is first inserted into an appropriate nucleic acid vector, that vector may be a plasmid, a virus or a linear DNA fragment, as desired. The vector may be naked, complexed with proteins or packaged in a delivery system such as a liposome, virosome, or a receptor mediated complex.

It is contemplated in the invention to express in specific cells a chimeric gene encoding a recombinant protein joined in-frame to a gly-containing sequence. The chimeric gene may be expressed in vivo or ex vivo as a result of introduction of genetic material containing the chimeric gene into cells which include but are not limited to stem cells, macrophages, T-cells, dendritic cells, cells of hematopoietic lineage, somatic cells and tumor cells. Techniques are known in the art for delivery of recombinant DNA to these cells. Such cells can be transfected ex vivo, i.e., after removal from the body, and then re-introduced into the body, or they can be targeted in vivo.

Transfer of a chimeric gene according to the invention can be accomplished through many means, including but not limited to DNA transfection using calcium phosphate coprecipitation, fusion of the target cell with liposomes containing the gene, erythrocyte ghosts or spheroplasts carrying the gene, plasmid and viral vector-mediated transfer, and DNA protein complex-mediated gene transfer such as receptor-mediated gene transfer.

1. Targeting of Cells Ex Vivo

For introduction of DNA into a cell ex vivo, a number of protocols for the transfection of various types of cells are known in the art.

Some transfection techniques involve the isolation of stem cells from total cell populations, as described in, for example, European patent applications 0 455 482 and 0 451 611. T-cell transfection is also described in Kasid et al., Proc. Nat. Aca. Sci., 1990, 87(1):473. Transfection of macrophages is described in Freas et al., Human Gene Therapy, 1993, 4(3):283, and in Krall et al., Blood, 1994, 83(9)L2737. Stem cell transfection is also described in Yu et al., Proc. Nat. Aca. Sci., 1995, 92(3):699, Lu et al., Human Gene Therapy, 1994, 5:203, Walsh et al. Proc. Soc. Exp. Biol. Med., 1993, 204:289; Weinthal et al. Bone Marrow Transplant.,1991, 8:403, Hamada et al., Jour. Immunol. Methods, 1991, 141:177.

Polylysine tagged with asialoglycoprotein may be used to complex and condense DNA and target the complex to hepatocytes (Wu and Wu, (1987) J. Biol. Chem. 262, 4429; U.S. Pat. No. 5,166,320). DNA transfer is believed to occur via the asialoglycoprotein tag specifically directing the complex to only those cells expressing the asialoglycoprotein receptor. Monoclonal antibodies also may be used to target DNA to particular cell types, as described in Machy et al., (1988) Proc. Natl. Acad. Sci. 85, 8027–8031; Trubetskoy et al., (1992) Bioconjugate Chem. 3, 323–7 and WO 91/17773, WO 92/19287. Lactosylated polylysine (Midoux et al (1993) Nucleic Acids Res. 21, 871–878) and galactosylated histones (Chen et al (1994) Human Gene Therapy 5, 429–435) have been shown to target plasmid DNA to cells bearing lectin receptors, and insulin conjugated to polylysine (Rosenkrantz et al (1992) Exp. Cell Res. 199, 323–329) to cells bearing insulin receptors.

2. Targeting of Cells In Vivo

In vivo cell targeting may be accomplished according to the invention using receptor-mediated gene transfer.

Receptor-mediated gene transfer is dependent upon the presence of suitable ligands on the surfaces of cells which will allow specific targeting to the desired cell type followed by internalization of the complex and expression of the DNA. One form of receptor-mediated gene transfer is wherein a DNA vector is conjugated to antibodies which target with a high degree of specificity for cell-surface antigens (Wong and Huang, 1987, Proc. Nat. Aca. Sci. 84:7851; Roux et al., 1989, Proc. Nat. Aca. Sci. 86::9079; Trubetskoy et al., 1992, Bioconjugate Chem. 3:323; and Hirsch et al., 1993, Transplant Proceedings 25:138). Nucleic acid may be attached to antibody molecules using polylysine (Wagner et al., 1990, Proc. Nat. Aca. Sci. 87:3410; Wagner et al., 1991, Proc. Nat. Aca. Sci. 89:7934) or via liposomes, as described below.

Increased expression of DNA derived from ligand-DNA complexes taken up by cells via an endosomal route has been achieved through the inclusion of endosomal disruption agents, such as influenza virus hemagglutinin fusogenic peptides, either in the targeting complex or in the medium surrounding the target cell.

Targeted gene delivery is also achieved according to the invention using a DNA-protein complex. Such DNA-protein complexes include DNA complexed with a ligand that interacts with a target cell surface receptor. Cell surface receptors are thus utilized as naturally existing entry mechanisms for the specific delivery of genes to selected mammalian cells. It is known that most, if not all, mammalian cells possess cell surface binding sites or receptors that recognize, bind and internalize specific biological molecules, i.e., ligands. These molecules, once recognized and bound by the receptors, can be internalized within the target cells within membrane-limited vesicles via receptor-mediated endocytosis. Examples of such ligands include but are not limited to proteins having functional groups that are exposed sufficiently to be recognized by the cell receptors. The particular proteins used will vary with the target cell.

Typically, glycoproteins having exposed terminal carbohydrate groups are used although other ligands such as antibodies or polypeptide hormones, also may be employed.

Generally, a ligand is chemically conjugated by covalent, ionic or hydrogen bonding to the nucleic acid. A ligand for a cell surface receptor may be conjugated to a polycation such as polylysine with ethylidene diamino carbodiimide as described in U.S. Pat. No. 5,166,320. DNA may be attached to an appropriate ligand in such a way that the combination thereof or complex remains soluble, is recognized by the receptor and is internalized by the cell. The DNA is carried along with the ligand into the cell, and is then expressed in the cell. The protein conjugate is complexed to DNA of a transfection vector by mixing equal mass quantities of protein conjugate and DNA in 0.25 molar sodium chloride. The DNA/protein complex is taken up by cells and the gene is expressed.

Liposomes have been used for non-viral delivery of many substances, including nucleic acids, viral particles, and drugs. A number of reviews have described studies of liposome production methodology and properties, their use as carriers for therapeutic agents and their interaction with a variety of cell types. See, for example, "Liposomes as Drug Carriers," Wiley and Sons, NY (1988), and "Liposomes from Biophysics to Therapeutics," Marcel Dekker, N.Y. (1987). Several methods have been used for liposomal delivery of DNA into cells, including poly-L-lysine conjugated lipids (Zhou et al., Biochem. Biophys. Acta. 1065:8–14, 1991), pH sensitive immunoliposomes (Gregoriadis, G., Liposome Technology, Vol I, II, III, CRC, 1993), and cationic liposomes (Felgner et al., Proc. Natl. Acad. Sci., USA, 84:7413–7417, 1987). Positively charged liposomes have been used for transfer of heterologous genes into eukaryotic cells (Felgner et al., 1987, Proc. Nat. Aca. Sci. 84:7413; Rose et al., 1991, BioTechniques 10:520). Cationic liposomes spontaneously complex with plasmid DNA or RNA in solution and facilitate fusion of the complex with cells in culture, resulting in delivery of nucleic acid to the cell. Philip et al. 1994, Mol. and Cell. Biol. 14:2411, report the use of cationic liposomes to facilitate adeno-associated virus (AAV) plasmid transfection of primary T lymphocytes and cultured tumor cells.

Delivery of an agent using liposomes allows for noninvasive treatment of diseases. Targeting of an organ or tissue type may be made more efficient using immunoliposomes, i.e., liposomes which are conjugated to an antibody specific for an organ-specific or tissue-specific antigen. Thus, one approach to targeted DNA delivery is the use of loaded liposomes that have been made target-specific by incorporation of specific antibodies on the liposome surface.

3. Viral Vector Mediated Gene Delivery

Recombinant viral vectors as well as other DNA transfer schemes can be used in practice of the present invention. A recombinant viral vector of the invention will include DNA of at least a portion of a viral genome which portion is capable of infecting the target cells and the transcription unit and control DNA sequence. By "infection" is generally meant the process by which a virus transfers genetic material to its host or target cell. Preferably, the virus used in the construction of a vector of the invention is also rendered replication-defective to remove the effects of viral replication on the target cells. In such cases, the replication-defective viral genome can be packaged by a helper virus in accordance with conventional techniques. Generally, any virus meeting the above criteria of infectiousness and capabilities of functional gene transfer can be employed in the practice of the invention.

Suitable viruses for practice of the invention include but are not limited to, for example, adenoviruses, adeno-associated virus, retroviruses, and vaccinia viruses, representative examples of which follow. Insertion of a chimeric gene of the invention into a viral vector involves conventional cloning sequences know to those of skill in the art.

Viral systems exploit the infectious capacity of viruses to introduce foreign DNA to eukaryotic cells with high efficiency. The gene of interest is cloned into the viral genome under the control of a promoter that is expressible in the selected host cell or organism. Recombinant vaccinia viruses, retroviruses and adenoviruses have often been used for DNA delivery purposes. A viral delivery vehicle is selected based on know advantages and disadvantages of its use. One of skill in the art will select a delivery vehicle weighing such by considerations in view of the intended therapeutic use of the non-immunogenic recombinant protein.

For example, integration of the viral vector into the host cell genome occurs after infection with a recombinant retrovirus. Such integration results in advantageous long-term expression of the transduced gene. However, retroviruses are limited in their use as vectors in that they infect only mitotic cells. Recombinant adenoviral vectors have the capacity to infect a wide spectrum of mitotic and postmitotic target cell but are maintained in the cell in episomal form, which may result in loss of the transduced gene in parallel with the cellular turnover. Recombinant vaccinia viral vectors can confer very high levels of expression of the transduced gene, and can infect a broad spectrum of target cells. However, this infection is often productive, resulting in rapid clearance of virus infected cells.

Described in detail below is the construction of recombinant vaccinia viruses retroviruses and adenoviruses, each carrying an influenza matrix chimeric gene of the invention.

a) Construction Of Recombinant Vaccinia Virus Containing Sequences Encoding Influenza Matrix/Gly-Containing Sequence Recombinant Protein.

Vaccinia virus recombinants carrying a selected protein coding sequence, for example, influenza matrix 1 protein, joined in-frame to a Gly-containing sequence are produced according to standard procedures (R J Murray et al. J.Exp.Med., 176:157, (1992)). A transfer vector may be constructed by cloning the influenza matrix cDNA/(GlyX)n chimeric gene into the viral vector. For example, the chimeric gene may be isolated on an EcoRI fragment from PGEM-matrix-(GlyX)n or pGEM-matrix-(E1 GlyX)n and cloned into the EcoRI site of pGS62 downstream of the vaccinia p7.5 early late promoter, which is the promoter of choice for expression of target proteins for CTL recognition (BEJ Coupar et al., Eur.J.Immunol., 16:1479, (1986)). Insert-containing plasmids are sequenced to determine correct orientation and reading frame alignment. Recombinant viruses are generated by transfection into wild-type-WR-strain-vaccinia infected TK-143 cells (S. Chakrabati et al., Mol. Cell. Biol., 5:3403 (1985)). Recombinants carrying insertions into the vaccinia thymidine kinase gene (TK) are selected in medium containing 25$\mu$g/ml BuDR. Viral stocks are prepared and titrated in CV-1 cells according to standard procedures.

A recombinant vaccinia vector encoding a matrix protein fused to a gly-containing sequence at the matrix protein carboxyl terminus is generated as described above, with two differences. First, the chimeric gene is excised from pGEM-matrix-(GlyX)n-COOH by HindIII-SfiI digestion. Second, cloning of the chimeric gene fragment into the EcoRI site of the vaccinia vector pGS62 is accomplished via blunt-end ligation after filling-in of both vector and insert ends with Klenow fragment or T4 DNA polymerase (for the SfiI end).

B) Construction Of A Recombinant Retrovirus Vector Containing Influenza Matrix/Gly-Sequence Repeat Chimeric Gene.

Recombinant retroviral vectors carrying a gene encoding a protein of interest or a chimeric gene encoding a recombinant protein of the invention are made as described by Trivedi et al., Int. Jour. Cancer 48:794, 1991. Described below, by way of example, is the construction of recombinant retroviral vector carrying a gene encoding the influenza matrix protein or a gene encoding influenza matrix/Gly-containing sequence recombinant protein.

The chimeric gene is excised from the pGEM-matrix (GlyX)n or pGEM-matrix(ElGlyX)n or pGEM-matrix (GlyX)nCOOH by HindIII and SalI digestion, and subcloned into the HindIII-XhoI site of the pCEP4 plasmid (Invitrogen), resulting in loss of the SalI and XhoI sites. The pCEP4-matrix and pCEP4-matrix(GlyX)n plasmids are then cleaved by SalI and SfiI to isolate fragments containing the matrix gene or influenza matrix chimeric gene, driven by the CMV promoter. After modification of the SalI 3' recessed ends by Klenow and the SfiI 3' protruding ends by T4 DNA polymerase, the isolated fragments are blunt-end ligated into the SnabI site of the pShis4 vector. Helper virus-free viral supernatants are then produced by transfection into the pA317 packaging cell line according to standard procedures (Miller et al., Mol. Cell. Biol. 6:2895, 1986).

c) Construction Of A Recombinant Adenovirus Vector Containing Influenza Matrix/Gly Sequence Chimeric Gene.

Recombinant adenoviral vectors carrying a gene encoding a protein of interest or a chimeric gene encoding a recombinant protein of the invention are made as follows. Described below, by way of example, is the construction of recombinant adenoviral vector carrying a gene encoding the influenza matrix protein or a gene encoding influenza matrix/(GlyX)n recombinant protein.

A SalI fragment containing the CMV promoter, the influenza matrix cDNA or influenza matrix chimeric gene and the SV40 polyA tail is excised from the pCEP4 matrix or the pCEP4-matrix(Gly-X)n plasmid and subcloned into the SalI site of the adenovirus transfer plasmid pΔE1sp1, containing adenovirus E1 sequences on both sides of the cloning site (Bett et al., Proc. Nat. Aca. Sci. 91:8802, 1994). Recombinant adenovirus is generated by homologous recombination between the pΔE1sp1-matrix or pΔE1sp1-matrix (GlyX)n plasmid and pJM17 containing a complete adenovirus-5 genome with a partially truncated E1 after cotransfection into Ad5 E1 expressing 293 cells (Graham et al., J.Gen, Virol, 36:59, 1977). Cotransfection, virus rescue, and propagation will be performed according to the standard methods (Graham et al., in Gene Transfer and Expression Protocols, E. J. Murray ed., Human a Press, Clifton, N.Y., p,109–128, 1991).

Expression of the chimeric gene may be detected by immunological methods, such as detection of the recombinant protein via immunofluorescence and immunoblotting using an antibody specific for the Gly-containing sequence and an antibody specific for the protein of interest. Alternatively, expression of the chimeric gene may be detected by an assay for the biological activity of that protein; for example, where the chimeric gene is a marker gene such as a NeoR chimera or a TK chimera, expression of the marker protein may be detected.

EXAMPLE III

How To Test For Evasion Of The Immune System

The procedures described in this example allow one of skill in the art to determine whether the presence of glycine-containing repetitive sequences influences the recognition of a foreign protein by the cellular immune system; i.e., confers non-immunogenicity on a protein which is immunogenic in the absence of the glycine repeat sequence.

Testing The Antigenicity And Immunogenicity Of Proteins Containing A Gly-Containing Repeat Sequence.

The effect of the presence of a Gly repeat sequence on processing/presentation of a protein which in its natural form is immunogenic may be tested according to in vitro and in vivo assays. By way of example, the immunogenicity of a recombinant influenza matrix protein 1 containing an inserted glycine-containing sequence is determined via in vitro and in vivo testing below.

An in vitro assay is dependent on the availability of polyclonal T-cell cultures or clones specific for the protein of interest and/or for identified target epitopes in a given protein, as described by Levitskaya et al. (Nature 375:685–688, 1995).

CTL epitopes useful in testing candidate recombinant proteins of the invention are known in the prior art. CTL epitopes are known for many different antigens, for example, for viral, bacterial and parasite antigens. In humans, such epitopes include but are not limited to the following:

i. The HLA A2 restricted epitope located in residues 57–68 of the influenza A matrix protein (Gotch et al., Nature, 326: 331–332, (1987); Moss et al., Proc.Natl.Acad.Sci. USA, 88: 8987–8990, (1991));

ii. The HLA B27 and B8 restricted epitopes in HIV p17 Gag and p24 Gag, respectively (Nixon et al., Nature, 336: 484–487, (1988); Nixon & McMichael, AIDS 5: 1049–1059, (1991));

iii. The HLA A2 restricted epitope in the EBV membrane protein LMP2 (Lee et al., J.Virol., 67: 7428–7235, (1993)); and iv. The HLA B53 restricted CTL epitope in the liver-stage-specific antigen (LSA-1) from P. falciparum (Hill et al., Nature, 360: 432–439, (1992)).

Examples of such epitopes in mouse systems include but are not limited to:

i. The H-2Kd restricted epitope in amino acids 249–260 of the plasmodium berghei circumsporozoite protein (Romero et al., Nature, 341: 323–325, (1989)). These CTLs can protect mice against parasitic infection; and ii. The H-2kD restricted epitope in animo acids 91–99 of the listeriolysin of Listeria monocytogenes (Palmer et al., Nature, 353: 852–855, (1991)).

The effect of the Gly-containing sequence on processing/presentation of these proteins will be performed following the strategy described herein for influenza matrix protein. That is, a chimeric protein that contains a Gly repeat sequence inserted within the protein relative to a known CTL epitope is expressed in cells of the appropriate MHC class I type using a viral or non-viral delivery system. Several such proteins may be tested, each having a different sequence inserted into the same site within the protein or having the same sequence inserted into different positions relative to the known CTL epitope. Thus, both the size of the gly-containing sequence required to achieve inhibition of antigen processing and the position of insertion of the repeat within the coding sequence relative to the CTL epitope may be determined.

To this end, repeats of different length and/or different sequence are inserted into a given protein. The repeats are inserted at the NH2 or COOH terminus of the protein of interest or within the coding sequence at various distances from the known epitope starting from immediately upstream or downstream of the epitope.

A chimeric gene encoding a recombinant protein of the invention comprising the influenza matrix protein 1 and a glycine-containing sequence is introduced and expressed in HLA A2 positive fibroblasts, EBV transformed lymphoblastoid cells lines (LCL), or mitogen-induced blasts according to gene delivery methods described herein. Chimeric gene expression is confirmed by immunofluoresence using an antibody specific for influenza matrix protein 1 and an antibody specific for the glycine-containing sequence. Chimeric gene expression also may be confirmed via Western blotting, according to standard procedures. A preparation comprising host cells expression the transduced chimeric gene is used as a target population in a cytotoxicity assay. Cytotoxic effector cells may be a polyclonal CTL population from an HLA A2 positive individual stimulated with autologous influenza A virus-infected cells or CTL clones specific for the 58–66 epitope, as described (Morrison et al., Eur. Jour. Immunol. 22:903, 1992).

Alternatively, immunological recognition of the transduced targets may be assessed by the capacity of these cells to induce production of lymphokines, such as TNF, INF, interleukins, etc., as taught by Asher et al., Jour. Immunol. 138:963, 1987. The following TNF assays are standard assays for testing for the presence of TNF in T cell supernatants. The L929 assay is based on the capacity of supernatants derived from cocultivation of T lymphocytes with cells expressing the relevant antigen to inhibit growth of TNF sensitive L929 cells.

Alternatively, immunological recognition of the transduced target cells is assessed via ELISA assays (R&D Systems, Mpls, MN) using a commercially available ELISA kit based on TNF-specific monoclonal antibodies.

An in vivo assay is based on the capacity of the protein of interest to induce rejection of transfected murine tumor cell lines in syngeneic hosts, as described be Trivedi et al., Int. J. Cancer 48:794 (1991). For example the immunogenicity of the influenza matrix protein and nonimmunogenicity of the matrix protein fused in-frame to a glycine-containing sequence, as described herein, may be tested as follows.

The S6C cell line, established from a spontaneous mammary carcinoma line originating in an ACA mouse (H-2f) (Kuzumaki et al., Europ. J. Cancer 39:471, 1987) is transfected with the pCEP matrix or pCEP matrix(GlyX)n plasmid. High levels of expression of the transfected gene is achieved using the CMV promoter to drive that gene. ACA mice are immunized with cells harboring one of the following: (1) no vector, (2) pCEP vector with no inserted chimeric gene, (3) PCEP plasmid containing the gene encoding the influenza matrix protein 1, and (4) pCEP matrix(Gly)n plasmid. See Trivedi et al., Int. Jour. Cancer 48:794, 1991. $1 \times 10^6$ cells, irradiated with 10,000 rads, are inoculated subcutaneously once a week for three consecutive weeks. Seven days after the last immunization and 24 hours before the viable cell challenge, the mice are irradiated with 400 rad to inhibit nonspecific immune reactions (Klein et al., Cold Spring Harbor Symp. Quant Biol. 27;463, 1962). Groups of 5–10 mice are challenged with graded numbers of viable cells/mouse, e.g., $10^3$–$10^6$ cells/mouse. Tumor growth is followed by weekly caliper measurement in 3 dimensions. The animals are dept under observation for a period of 8 weeks after challenge. The mean tumor load is calculated by adding the individual tumor diameters and dividing the sum by the total number of mice in the group. The statistics of tumor take is calculated according to the Fisher's exact test.

EXAMPLE IV

EBNA1 Glycine-Containing Repeat Sequence

In one embodiment of the invention, a repetitive nucleic acid sequence encoding a polypeptide corresponding to the Epstein-Barr virus nuclear antigen (EBNA)1 internal gly-ala repeat sequence, or functional derivatives thereof, is inserted into a gene encoding a protein of interest. The gene is then transferred into and expressed in a host cell such that the expressed recombinant, glycine sequence-containing polypeptide is non-immunogenic, i.e., is not recognized by cytotoxic T lymphocytes.

According to the invention, a polypeptide corresponding to the Epstein Barr Virus nuclear antigen (EBNA) 1 internal gly-ala repeat (amino acid 89–327 of the prototype B95.8 EBV strain) is shown in FIG. 1. A recombinant protein is formed by placing this polypepide within a selected site in an antigenic protein to render the protein non-antigenic.

The Epstein-Barr virus (EBV) encoded nuclear antigen (EBNA)1 is expressed in latently EBV infected B-lymphocytes that persist for life in healthy virus carriers (Tierney, R. J. at al J. Virol. 68, 7374–7385 1994), and is the only viral protein regularly detected in all EBV associated malignancies (reviewed in Masucci, M. G. & Ernberg, I. Trends in Microbiology 2, 125–130, 1994, Klein, G. Cell 77, 791–793, 1994). Major histocompatibility complex (MHC) class 1 restricted, EBNA1-specific cytotoxic T lymphocyte (CTL) responses have not been demonstrated (reviewed in Masucci, M. G. & Ernberg I. Trends in Microbiology 2, 125–130, 1994, Rickinson, A., et al. in A New Look at Tumor Immunology, eds. McMichael, A & Franks, L, pp 53–80, CSHL Press, New York, 1992) suggesting that this viral antigen may have evolved the capacity to escape immune responses.

EBNA1 is a phosphoprotein (Rawlins, D. R. el al. Cell 42, 859–868, 1985) composed of unique N- and C-terminal domains (amino acids 1–89 and 327–641, respectively, in the prototype B95.8 EBV strain) joined by a repetitive sequence of arg-gly containing motifs surrounding an internal gly-ala repeat (Baer, R., et al. Nature 310, 207–211, 1984) (FIG. 1).

It has been observed that Gly-ala repeats of different lengths are present in all EBV isolates, and represent the major target of EBNA specific antibody responses. However, the function of the gly-containing sequence was previously unknown. The experiments described below were designed to test whether the presence of the repetitive sequence which encompasses more than one third of the ENBA1 molecule, influences the recognition of EBNA1 by the cellular immune system.

EXAMPLE V

Insertion Of Foreign Epitopes Into EBNA1

Taking advantage of the observation that EBV induced CTL responses in Caucasian HLA A11 positive individuals are often dominated by All-restricted reactivities to peptide epitopes corresponding to residues 399–408 and 416–424 of the EBNA4 protein (Gavioli, R., et al.J. Virol. 67, 1572–1578, 1993, de Campos-Limas, P. O., et al.J. Exp Med. 179, 1297–1305, 1994), the immunodominant EBNA4 416–424 epitope was inserted in frame within the intact EBNA1 sequence, or within EBNA1 deletion mutants that did not contain the glycine-alanine repeats (FIG. 2). The generation of vaccinia virus recombinants carrying the coding sequences of the EBNA1 and EBNA4 (also known as EBNA-3B) genes from the B95-8 virus has been described previously (Murray, R., et al J. Exp Med. 176, 157–168, 1992). Chimeric proteins containing the HLA A11 restricted EBNA4 416–424 epitope (IVTDFSVIK, E4) (SEQ ID NO:67) within EBNA1 (E1), or an EBNA1 deletion mutant that lacks the internal glycine-alanine repeat region (E1ΔGA) were produced by inserting an oligonucleotide corresponding to the E4 epitope into various positions within the EBNA1 coding sequence.

The pBS-E1ΔGA & the pBS-E1ΔGA plasmids, encoding the full length open reading frame of the EBNA1 gene and the deletion mutant, respectively were opened at the NcoII site (genomic position: 108067), or the NcoI site, the PflMI site (gp: 109291), or Bsu361 site (gp:109510). For insertion into the NcoI site, two oligonucleotides (E1N-E4F: 5'-CATGCCATAGTAACTGACTTTAGTGTAATCAAG-3' (SEQ ID NO: 57) and E1N-E4R: 5'-CATGCTTGATTACACTTAAGTCAGTTACTAT-3' (SEQ ID NO:58) were annealed in 50 mM NaCl, 10 mM $MgCl_2$, 50 mM Tris-HCl, pH 8.0 at a concentration of 10 mM in a volume of 20 μl by heating to 97° C. for 5 minutes followed by slow cooling to 50° C. and incubation at 37° C. for an additional 5 minutes. After annealing, dGTP was added to a concentration of 100 mM along with 3U of T4 DNA polymerase and incubated at 12° C. for 20 minutes. EDTA was then added to 10 mM, followed by heating at 75° C. for 10 minutes and dilution to a final volume of 100 μl. The oligo was then ligated to NcoI digested pBS- E1 and pBS-E1ΔGA at a ratio of 100:1. For insertion into the PflMI site, oligos E1P-E4F (5'-CGATCGTAACTGACTTTAGTGTAATCAGG-3') (SEQ ID NO:59) and E1P-E4R (5'-CCTTGATTACACTAAAGTCAGTTACGATCGTGC-3') (SEQ ID NO:60) were annealed and ligated to the PflMI site of pBS-E1ΔGA as above. E1P-E4F and E1P-E4R were designed with a unique PvuI site for identification purposes and can only insert in the proper orientation. For insertion into the Bsu36I site, oligos E1B-E4F (5'-TAACGATCGTAACTGACTTTAGTGTAATCAAGG-3' (SEQ ID NO:61)) and E1B-E4R (5'TTACCTTGATTACACTAAGTCAGTTACGATCG-3' (SEQ ID NO:62)) were annealed and ligated into the Bsu36I site of pBS-E1DGA as described above. After electroporation, plasmids containing inserts were screened by polymerase chain reaction of minipreps and sequenced to determine correct orientation and ensure complete fidelity throughout manipulations.

Following isolation of oligo insertion sequences, the E1 and E1ΔGA open reading frames were excised by BstYI and HincII digestion. The ends of the isolated DNA fragments were repaired with T4 DNA polymerase and inserted at the SmaI site of pSC11. Due to the toxicity of the EBNA1 glycine-alanine repeats for vaccinia virus replication, only recombinants containing the pBS-E1 chimera inserted in negative orientation with respect to the P7.5 promoter were selected. For pBS-E1ΔGA chimeras, both positive and negative orientation inserts were selected.

Recombinant vaccinia viruses were generated by transfection of the above-described plasmids into WR-strain-wild-type-vaccinia infected TK-143 cells and viral stocks were prepared and titrated in CV-1 cells, as previously described (Murray, R., et al. J. Exp. Med. 176, 157–168, 1992).

The capacity of recombinant vaccinia viruses to sensitize HLA A11 positive targets to lysis by EBNA4 416–424 epitope specific CTLs was tested according to standard methods. Semi-confluent monolayers of fibroblasts from donor QJZ (HLA A11 B13,B51) were grown in 96 wells microliter plates (Costar), infection was carried out for 12 hr at a m.o.i. of 10 in the assay wells in the presence of 3 $\mu$/Ci $^{51}$NaCrO$_4$ (Amersham) per well. Alternatively, infection was carried out for different times starting from 24 hr before addition of the effectors. HLA-A11 restricted EBNA4-specific CTL clones were obtained by stimulation of lymphocytes from the EBV seropositive donors BK (HLA A2,A11 B7,B35) with the autologous B95.8 virus transformed lymphoblastoid cell line (LCL). Single cell cloning was done by limiting dilution.

The specificity of the CTL clones for the EBNA4 416–424 epitope was assessed by their capacity to lyse HLA A11 positive PHA blasts preincubated with $10^{-10}$M of the corresponding synthetic peptide. The cytoxic activity was assayed in triplicates in standard 4 hr $^{51}$Cr release assays.

Figure 3:
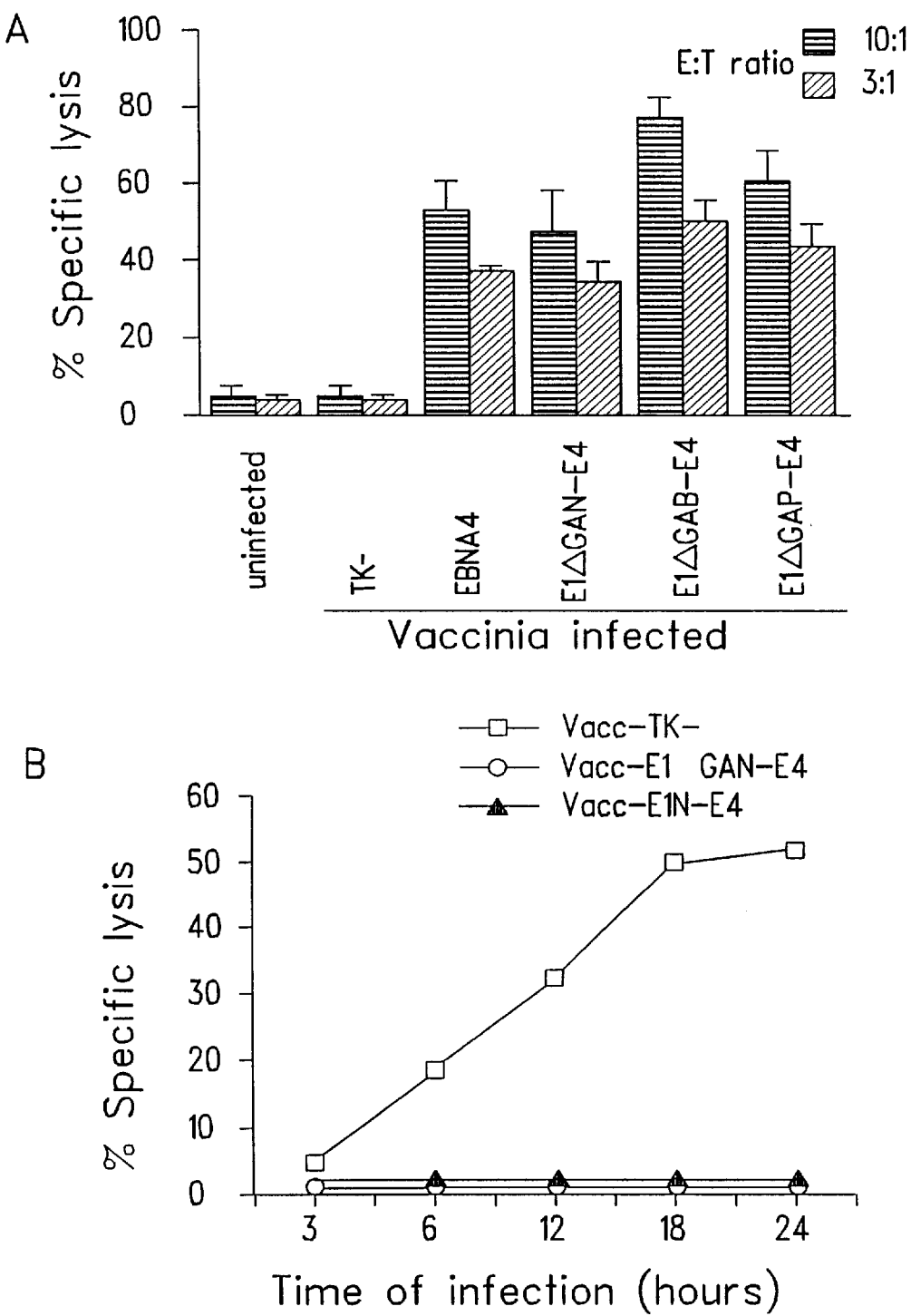
FIGS. 3A and 3B show results of sensitization of HLA A11 positive fibroblasts infected with vaccinia recombinants expressing the gly-ala deletion mutants and full size EBNA1 chimeras to lysis by A11-restricted CTLs specific for the EBNA4 416–424 epitope. Fibroblasts expressing the gly-ala deleted chimeras were lysed as efficiently as fibroblasts expressing the intact EBNA4 whereas fibroblasts expressing the full size EBNA1 chimera were not killed. A. lysis of fibroblasts expressing the intact EBNA4 protein (Vacc-EBNA4), or EBNA1 deletion mutants containing the EBNA4 416–424 epitope inserted at the NcoI (Vacc-E1ΔGAN-E4), Pf1MI (Vacc-E1ΔGAP- E4) or Bsu36I sites (Vacc-E1ΔGAB-E4). Mean and SE of 4 experiments. B. lysis of fibroblasts infected for different lengths of time with the Vacc-E1ΔGAN-E4 recombinant of with the Vacc-E1N-E4 recombinant that contains the intact EBNA1 chimera. The % specific lysis at 10:1 effector:target ratio in one representative experiment out of three is shown in the figure.
Figure 4:
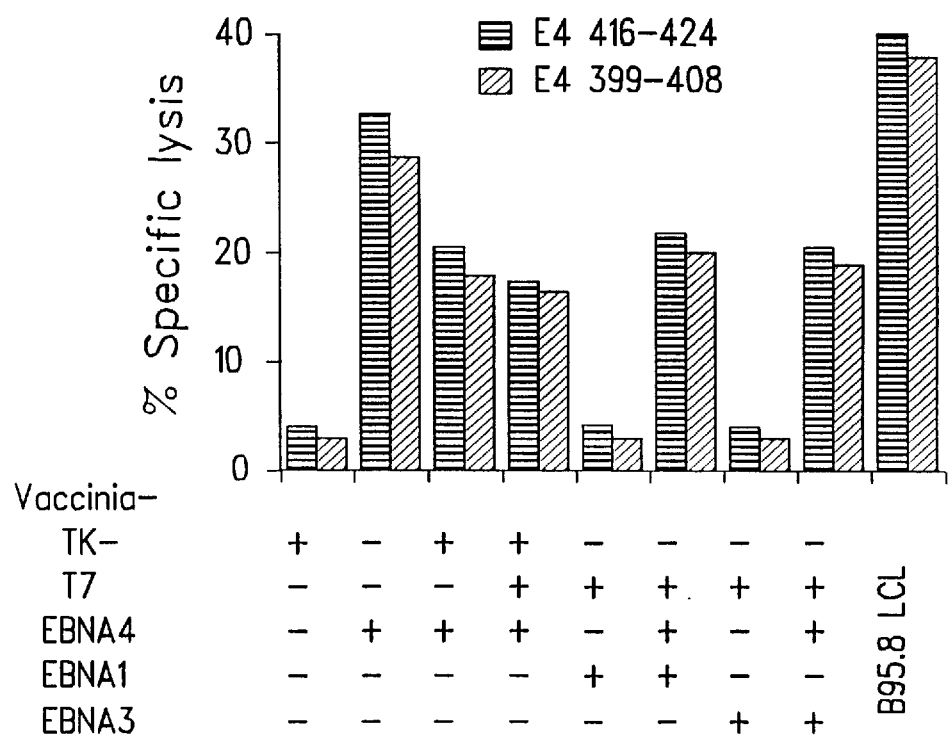
FIG. 4 demonstrates that over-expression of an intact EBNA1 protein does not inhibit processing of EBNA4 and presentation of the 399–408 and 416–424 epitopes. Lysis of HLA All positive fibroblasts expressing EBNA4, EBNA1 or EBNA3 or coexpressing EBNA1+EBNA4 and EBNA3+EBNA4 by CTLs specific for the EBNA4 399–408 (grey box) and 416–424 (black box) epitopes. The % specific lysis at 10:1 effector:target ratio of one representative experiment out of three is shown in the figure.
Figure 5:
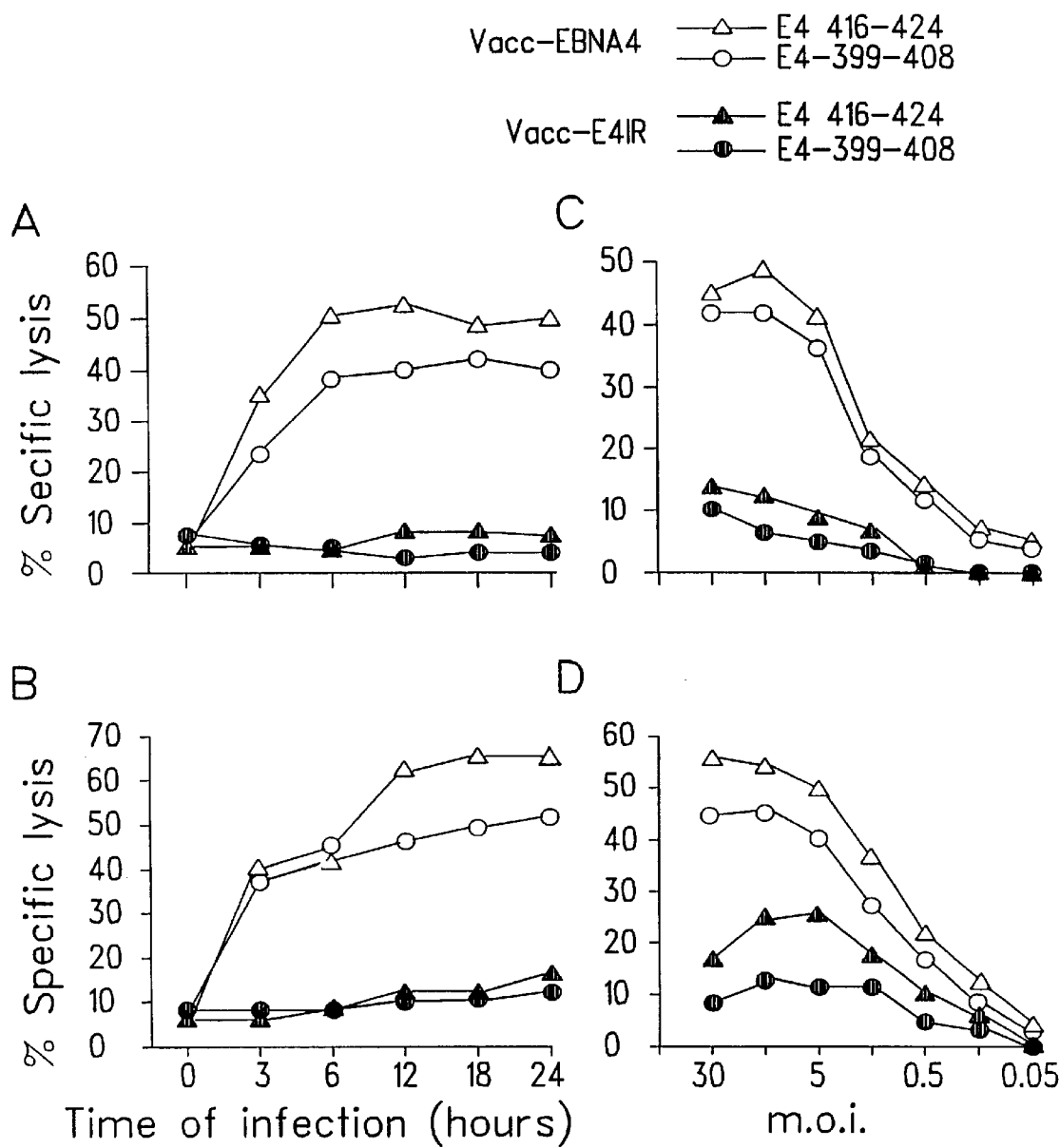
FIGS. 5A–5D show results of sensitization of HLA All positive cells expressing EBNA4 or the E4IR chimera to lysis by A11-restricted CTLs specific for the EBNA4 399–408 and 416–424 epitopes. HLA All positive fibroblasts (FIGS. 5A and 5C) or the QJZsp LCL that carries a Chinese EBV isolate with mutations that abrogate HLA All restricted recognition of the endogenous EBNA4 protein (FIGS. 5B and 5D), were infected with the Vacc-EBNA4 (open triangle, open circle) or Vacc-E4IR (closed triangle, closed circle) recombinants at a m.o.i. for the indicated times (FIGS. 5A and 5B) or at the indicated m.o.i. for 12 hrs (FIGS. 5C and 5D) before use as targets for A11-restricted CTLs specific for the EBNA4 399–408 (open circle, closed circle) or 416–424 (open triangle, closed triangle) epitopes. The % specific lysis recorded at 10:1 effector:target ratio in one representative experiment out of three performed with each effector:target combination is shown in the figure.

EBNA1 deletion mutants containing the EBNA4 416–424 epitope inserted at the his39, pro446, or lys520 positions, relative to the B95.8 sequence (Vacc-E1ΔGAN-E4, Vacc-E1ΔGAP-E4 and Vacc-E1ΔGAB-E4, respectively) sensitized HLA A11 positive fibroblasts to lysis by EBV-specific CTLs (FIG. 3A). The level of killing was in each case comparable to that observed after infection with a vaccinia recombinant expressing EBNA4. In contrast, fibroblasts expressing a chimeric full size EBNA1 with the EBNA4 416–424 epitope inserted at his39 (Vacc-E1N-E4) were not recognized by the CTLs (FIG. 3B). The differing recognition of Vacc-E1ΔGAN-E4 and Vacc-E1N-E4 infected cells supports the view that presence of the gly-ala repeats is directly involved in the failure of the E1N-E4 chimera to sensitize target cells to lysis.

EXAMPLE VI

The Effects Of Over-Expression Of EBNA1 On Recognition Of A Foreign Protein

The following experiments were performed in order to test whether over-expression of EBNA1 could influence antigen processing/presentation of other antigenic proteins expressed in the same target cell. High levels of EBNA1 were expressed in vaccinia virus infected cells through the use of an inducible T7 RNA polymerase system (Murray, R., et al.J. Exp. Med. 176, 157–168, 1992). HLA All positive fibroblasts infected for 12 hr with Vacc-T7 and Vacc-EBNA1 or, as controls, Vacc-T7 and Vacc-EBNA3 (Murray, R., et al.J. Exp. Med. 176, 157–168. 1992) were superinfected for 6 hr with Vacc-EBNA4 and then tested for sensitivity to lysis by CTLs specific for the 399–408 or 416–424 epitopes (FIG. 4). Over-expression of EBNA1 or EBNA3 did not prevent recognition of the Vacc-EBNA4 infected fibroblasts although a 30 to 50% reduction of lysis was observed compared to the Vacc-EBNA4 control, probably due to competition of the viruses for the cellular transcription/translation machinery. Thus, the gly-ala repeat structure does not function as a trans-acting inhibitor of antigen processing/presentation.

It is concluded that presence of the Gly-containing sequence within the context of the target protein generates a signal which either prevents processing MHC class I antigen or, alternatively, sequesters the processing products to a cellular compartment which is inaccessible to MHC class I restricted presentation. Thus, failure to undergo antigen processing and MHC class I restricted presentation affords evasion of the immune system independently of the class I type of the host.

EXAMPLE VII

Insertion Of EBNA1 Glycine-Containing Sequence Into A Foreign Antigenic Protein The following experiments were performed in order to demonstrate that insertion of the EBNA1 gly-ala repeats into an antigenic protein prevents recognition by the immune system of cells expressing the recombinant protein. A recombinant vaccinia virus expressing a chimeric EBNA4 protein that contains the gly-ala sequence (FIG. 2) was produced. The pBS-E4IR plasmid was constructed by inserting an EBNA1 fragment extending from the Ncol site (genomic position(gp): 108067) to the Apal site (gp: 109261) encompassing the internal gly-ala repeat region with flanking residues at the amino and carboxyl sides (IR, amino acid 39 to 437 relative to the B95.8 EBNA1 sequence) into the Msel site of EBNA4 (gp: 97302) between amino acid residues trp624 and pro625. A clone of correct orientation was sequenced to ensure proper reading frame alignment. The EBNA4IR open reading frame (E4IR, was excised by EcoRI and SstI, the ends were repaired, and ligated into the Smal site of pSC11. A clone of negative orientation relative to the P7.5 promoter was selected. Recombinant vaccinia viruses were generated by transfection of the above plasmids into WR-strain-wild-type-vaccinia infected TK-143 cells and viral stocks were prepared and titrated in CV-1 cells as previously described (Murray, R., et al. J. Exp. Med. 176, 157–168 1992). HLA All positive cells infected with the Vacc-EBNA4 and Vacc-E4IR recombinants were assayed for expression of the recombinant proteins and for sensitivity to lysis by CTLs specific for the EBNA4 399–408 and 416–424 epitopes. Judging from the percentage positive cells and intensity of fluorescence detected in experiments performed over a wide range of m.o.i., the recombinant proteins were expressed with identical kinetics and at similar levels (Levitskaya et al., Nature 375:685–688, 1995). HLA All positive fibroblasts infected with Vacc-EBNA4 were sensitized to lysis by CTL clones specific for the 399–408 or 416–424 epitopes with maximal lysis after for 6 hrs (FIG. 5A) at a m.o.i. of 5 (FIG. 5C). In contrast, cells infected with Vacc-E4IR were lysed only weakly, even after infection at 6 fold higher m.o.i. or for prolonged periods of time. Infection of the QJZsp LCL that carries a Chinese EBV isolate with selective mutations aborting the recognition of the endogenous EBNA4 399–408 and 416–424 epitopes gave essentially similar results (FIGS. 5B and 5D). It is concluded that the presence of the gly-containing sequence within the antigenic protein of interest inhibits processing and MCH class I restricted presentation independently of the cell lineage of the target cells. The results demonstrate that the gly-containing sequence functions as a cis-acting inhibitor of antigen processing-presentation.

USE

The invention provides for avoiding an undesired immune response directed to a recombinant protein, e.g., i. antigenic proteins to be expressed in cells of human or other species for gene therapy purposes; ii. antigenic structural or regulatory proteins of transfer vectors used for the above purposes; and iii. components of vaccines which are not intended to be antigenic.

Insertion of a nucleic acid sequence coding for the glycine-containing polypeptide, or functional derivatives thereof, can be used for modifying genes encoding therapeutic proteins, marker genes, regulatory proteins of viral vectors, or vaccine components. Therapeutic proteins to be expressed in mammalian cells include but are not limited to, e.g., enzymes, cytokines, lymphokines, cell adhesion molecules, costimulatory molecules or protein products of drug resistance genes or tumor suppressor genes. Marker genes include but are not limited to, e.g., neoR, multidrug resistance gene, thymidine kinase gene, β-galactosidase, dihydrofolate reductase (DHFR) and chloramphenicol acetyl transferase gene that can be inserted into cells together with a therapeutic gene or separately. For example, tumor-specific CTLs may contain a marker gene and thus be tagged with the encoded marker protein. This embodiment of the invention is useful in those cases in which a marker protein is immunogenic and thus may severely diminish the therapeutic efficacy of the CTL. Once injected into a patient, the progress of the tagged CTL to the tumor site may be followed via the marker, and the marker itself is rendered non-immunogenic according to the invention. The marker gene and the therapeutic gene also may be one and the same.

Structural or regulatory proteins of viruses are often immunogenic in patients. Such proteins are often encoded by viral vectors that are used or developed for purpose of gene therapy; for example, vectors based on vaccinia virus, adenovirus, herpesvirus or retroviruses. Components of vaccines useful as recombinant proteins of the invention include those vaccine components which are necessary for effective vaccination, but are desired as non-antigenic vaccine components, for example, vaccine structural components such as envelop, capsid, or regulatory proteins of viral, bacterial or parasitic infections, or components of cancer vaccines. By rendering certain components of the vaccine non-immunogenic, it is believed that the host immune response will be more effective against the immunogenic components of the vaccine.

DOSAGE AND PHARMACEUTICAL FORMULATIONS

A patient that is a afflicted with viral or genetic disease may be treated in accordance with the invention via in vivo or ex vivo methods. For example in in vivo treatments, a recombinant nucleic acid or protein of the invention can be administered to the patient, preferably in a biologically compatible solution or a pharmaceutically acceptable delivery vehicle, by ingestion, injection, inhalation or any number of other methods. The dosages administered will vary from patient to patient; a "therapeutically effective dose" is determined by the level of enhancement of function of the transferred genetic material balanced against any risk or deleterious side effects. Monitoring levels of gene introduction, gene expression and/or the presence or levels of the encoded recombinant protein will assist in selecting and adjusting the dosages administered. Generally, a composition including a recombinant protein, as described herein, is administered in a single dose in the range of 10 ng –100 μg/kg body weight, preferably in the range of 100 ng –10 μg/kg body weight.

While the invention has been described with respect to certain specific embodiments, it will be appreciated that many modifications and changes may be made by those skilled in the art without departing from the spirit of the invention. It is intended, therefore, by the appended claim to cover all such modifications and changes as fall within the true spirit and scope of the invention.

OTHER EMBODIMENTS

Other embodiments will be evident to those of skill in the art. It should be understood that the foregoing detailed description is provided for clarity only and is merely exemplary. The spirit and scope of the present invention are not limited to the above examples, but are encompassed by the following claims.

TABLE 1

Primers for multimerization of minimal motivs

| SEQ ID No. | | primer sequence | SEQ ID No. | minimal motiv |
|---|---|---|---|---|
| 2 | ZGA1 | 5'GGAGCTGGTGCTGGAGGTGCGGGT3' | 3 | G A G A G G A G |
| 4 | ZGA2 | 5'CTCCACCCGCACCTCCAGCACCAG3' | | GGA GCT GGT GCT GGA GGT GCG GGT |
| | | | | GA CCA CGA CCT CCA CGC CCA CCT C |
| 5 | ZGS1 | 5'GGAAGTGGAGCTGGAGGTGCGGGT3' | 6 | G S G A G G A G |
| 7 | ZGS2 | 5'TTCCACCCGCACCTCCAGCTCCAC3' | | GGA GGT GGA GCT GGA GGT GCG GGT |
| | | | | CA CCT CGA CCT CCA CGA CCA CCT T |
| 8 | ZGR1 | 5'GGAAGAGGAGCTGGAGGTGCGGGT3' | 9 | G R G A G G A G |
| 10 | ZGR2 | 5'TTCCACCCGCACCTCCAGCTCCTC3' | | GGA AGA GGA GCT GGA GGT GCG GGT |
| | | | | CT CCT CGA CCT CCA CGA CCA CCT T |

TABLE 1-continued Primers for multimerization of minimal motivs

| SEQ ID No. | | primer sequence | SEQ ID No. | minimal motiv |
|---|---|---|---|---|
| 11 | ZGE1 | 5'GGAGAAGGAGCTGGAGGTGCGGGT3' | 12 | G   E   G   A   G   G   A   G<br>GGA GAA GGA GCT GGA GCT GCG GGT<br>    TT  CCT CGA CCT CCA CGC CCA CCT C |
| 13 | ZGE2 | 5'CTCCACCCGCACCTCCAGCTCCTT3' | | |
| 14 | ZGY1 | 5'GGATATGGAGCTGGAGGTGCGGGT3' | 15 | G   Y   G   A   G   G   A   G<br>GGA TAT GGA GCT GGA GGT GCG GGT<br>    TA  CCT CGA CCT CCA CGC CCA CCT A |
| 16 | ZGY2 | 5'ATCCACCCGCACCTCCAGCTCCAT3' | | |
| 17 | ZMGS1 | 5'GGATCAGGCAGCGGAGGTAGCGGT3' | 18 | G   S   G   S   G   G   S   G<br>GGA TCA GGC AGC GGA GGT AGC GGT<br>    GT  CCG TCG CCT CCA TCG CCA CCT A |
| 19 | ZMGS2 | 5'ATCCACCGCTACCTCCGCTGCCTG3' | | |
| 20 | ZMGR1 | 5'GGACGTGGCCGAGGAGGTAGAGGT3' | 21 | G   R   G   R   G   G   R   G<br>GGA CGT GGC CGA GGA GGT AGA GGT<br>    CA  CCG GCT CCT CCA TCT CCA CCT G |
| 22 | ZMGR2 | 5'GTCCACCTCTACCTCCTCGGCCAC3' | | |
| 23 | ZMGE1 | 5'GGAGAGGGCGAAGGAGGTGAAGGT3' | 24 | G   E   G   E   G   G   E   G<br>GGA GAG GGC GAA GGA GGT GAA GGT<br>    TC  CCG CTT CCT CCA CTT CCA CCT C |
| 25 | ZMGE2 | 5'CTCCACCTTCACCTCCTTCGCCCT3' | | |

TABLE 2

Coding capacity of gly—ala polymers

| primer set | positive orientation | | | | | | | | negative orientation | | | | | | | |
|---|---|---|---|---|---|---|---|---|---|---|---|---|---|---|---|---|
| ZGA | gly | ala | gly | ala | gly | gly | ala | gly [SEQ ID NO: 3] | leu | his | pro | his | leu | gln | his | gln [SEQ ID NO: 68] |
| ZG5 | gly | ser | gly | ala | gly | gly | ala | gly [SEQ ID NO: 6] | phe | his | pro | his | leu | gln | leu | his [SEQ ID NO: 69] |
| ZGR | gly | arg | gly | ala | gly | gly | ala | gly [SEQ ID NO: 9] | phe | his | pro | his | leu | gln | leu | leu [SEQ ID NO: 70] |
| ZGE | gly | glu | gly | ala | gly | gly | ala | gly [SEQ ID NO: 12] | leu | his | pro | his | leu | gln | leu | leu [SEQ ID NO: 71] |
| ZGY | gly | tyr | gly | ala | gly | gly | ala | gly [SEQ ID NO: 15] | ile | his | pro | his | leu | gln | leu | his [SEQ ID NO: 72] |
| ZMGS | gly | ser | gly | ser | gly | gly | ser | gly [SEQ ID NO: 18] | ile | his | arg | tyr | leu | arg | cys | leu [SEQ ID NO: 73] |
| ZMGR | gly | arg | gly | arg | gly | gly | arg | gly [SEQ ID NO: 21] | val | his | leu | tyr | leu | leu | gly | his [SEQ ID NO: 45] |
| ZMGE | gly | glu | gly | glu | gly | gly | glu | gly [SEQ ID NO: 24] | leu | his | leu | his | leu | leu | arg | pro [SEQ ID NO: 64] |

TABLE 3

Cloning of gly—ala repeats into the Sma I site of pGEX-2T i. digestion of pGEX-2T with Sma I:
                BamHI Sma I EcoRI
[SEQ ID NO: 26]  GTT GGATCC CCCGGG AATTC ATCGT
                CAA CCTAGG GGGCCC TTAAG TAGCA
                GTT GGATCCCC GGGAATTC ATCGT
                CAA CCTAGGGG CCCTTAAG TAGCA ii. modification of the ends of the gly—ala polymer with Klenow:
[SEQ ID 27]      GGA GCT GGT N...N GCG GGT
                GA CCA N...N CGC CCA CCT C
                GGA GCT GGT N...N GCG GGT GGA G [SEQ ID 30]
                CCT CGA CCA N...N CGC CCA CCT C

TABLE 3-continued

Cloning of gly—ala repeats into the Sma I site of pGEX-2T iii. Insertion of gly—ala into the pGEX-2T Sma I site:

| | pGEX-2T | gly—ala repeat | pGEX-2T |
|---|---|---|---|
| [SEQ ID 28] | GTTGGATCCCC | GGA GCT GGT N...N GCG GGT GGA G | GGGAATTCATCGT [SEQ ID 31] |
| | CAACCTAGGGG | CCT CGA CCA N...N CGC CCA CCT C | CCCTTAAGTAGCA |

TABLE 4

Cloning of gly—ala repeats into the Rsa I site of the influenza A matrix protein:

i. preparation of the pGEM-matrix plasmid:
Rsa I digestion [SEQ ID NO: 29]  GAA ACG T  AC GTT CTC
　　　　　　　　　　　　　　　　CTT TGC A  TG CAA GAG ii. isolation and preparation of the gly—ala repeat:

| | pGEX-2T | gly—ala repeat | pGEX-2T |
|---|---|---|---|
| [SEQ ID NO: 28] | GTTGGATCCCC | GGA GCT GGT N...N GCG GGT GGA C | GGGAATTCATCGT [SEQ ID NO: 31] |
| | CAACCTAGGGG | CCT CGA CCA N...N CGC CCA CCT C | CCCTTAAGTAGCA |

Bam HI
　　　　　　　　　　GATC CCC  GGA GCT GGT N...N GCG GGT GGA G  GGGAATTCATCGT
　　　　　　　　　　　　 GGG  CCT CGA CCA N...N CGC CCA CCT C  CCCTTAAGTAGCA partial filling with A and G nucleotites (Klenow):
　　　　　　　　　　GATC CCC  GGA GCT GCT N...N GCG GGT GGA G  GGGAATTCATCGT
　　　　　　　　　　　AG GGG  CCT CGA CCA N...N CGC CCA CCT C  CCCTTAAGTAGCA Eco RI
　　　　　　　　　　GATC CCC  GGA GCT GGT N...N GCG GGT GGA G  GGG
　　　　　　　　　　　AG GGG  CCT CGA CCA N...N CGC CCA CCT C  CCCTTAA mung bean nuclease
　　　　　　　　　　　TC CCC  GGA GCT GCT N...N GCG GGT GCA C  GGG
　　　　　　　　　　　AG GGG  CCT CGA CCA N...N CGC CCA CCT C  CCC iii. insertion of gly—ala encoding repeat into the matrix protein:

| | matrix | gly—ala repeat | | matrix |
|---|---|---|---|---|
| [SEQ ID NO: 33] | GAA ACG T TC CCC | GGA GCT GGT N...N GCG GGT GGA | G GGG | AC GTT CTC [SEQ ID NO: 32] |
| | CTT TGC A AGGGG | CCT CGA CCA N...N CGC CCA CCT C | C CCC TG | CAA GAG |

TABLE 5

Cloning of gly—ala repeats into the Bam H I site of the influenza A matrix protein:

i. modification of the Bam H I site in the matrix protein:
BamHI
　　　　　　[SEQ ID NO: 34]  AAC GGG　　　　　　　　　　　　　　　　　　　　GAT CCA AAT AAC

TABLE 6

Cloning of gly—ala repeats into the Stu 1 site of the influenza A matrix protein:

i. digestion of the pGEM Matrix plasmid with Stu I:
   [SEQ ID NO: 39] TTG CAG G CC TAT CAG
                   AAC GTC C GG ATA GTC ii. isolation of the GlyAla cassete
   [SEQ ID NO: 28] GTTGGATCCCC GGA GCT GGT N...N GCG GGT GGA G  GGGAATTCATCGT [SEQ ID NO: 31]
                   CAACCTAGGGG CCT CGA CCA N...N CGC CCA CCT C  CCCTTAAGTAGCA
                   Bam HI
                   GATC CCC GGA GCT GGT N...N GCG GGT GGA G  GGGAATTCATCGT
                        GGG CCT CGA CCA N...N CGC CCA CCT C  CCCTTAAGTAGCA
   partial filling with A and G nucleotites (Klenow):
                   GATC CCC GGA GCT GGT N...N GCG GGT GGA G  GGGAATTCATCGT
                   AG GGG CCT CGA CCA N...N CGC CCA CCT C    CCCTTAAGTAGCA
   Eco RI
                   GATC CCC GGA GCT GGT N...N GCG GGT GGA G  GGG
                   AG GGG CCT CGA CCA N...N CGC CCA CCT C    CCCTTAA
   mung bean nuclease
                   TC CCC GGA GCT GGT N...N GCG GGT GGA G  GGG
                   AG GGG CCT CGA CCA N...N CGC CCA CCT C  CCC iii. insertion of gly—ala coding repeat into the matrix protein:
                   matrix           gly—ala repeat                        matrix [SEQ ID NO: 36].
   [SEQ ID NO: 40] TTG CAG G TC CCC GGA GCT GGT N...N GCG GGT GGA  G GGG CC TAT CAG
                   AAC GTC C AG GGG CCT CGA CCA N...N CGC CCA CCT  C CCC GG ATA GTC

TABLE 7

Cloning of gly—ala repeats downstream of the matrix protein:

i. preparation of matrix DNA by PCR amplification
   product:
   [SEQ ID NO: 41] ATAAAGCTT ATG AGT N...N TTC AAG TGGATCCTCG   [SEQ ID NO: 37]
                   TATTTCGAA TAC TCA N...N AAG TTC ACCTAGCAGC
   Hind III-Bam H I digestion of PCR amplified matrix DNA:
                   AGCT ATG AGT N...N TTC AAG TG
                        A TAC TCA N...N AAC TTC ACCTAG ii. isolation of the GlyAla cassete
                   PGEX-2T     gly—ala repeat                         pGEX-2T
   [SEQ ID NO: 28] GTTGGATCCCC GGA GCT GGT N...N GCG GGT GGA G  GGGAATTCATCGT [SEQ ID NO: 31]
                   CAACCTAGGGG CCT CGA CCA N...N CGC CCA CCT C  CCCTTAACTAGCA
   Eco RI digestion of pGEX-(GlyAla)n
                   GTTGGATCCCC GGA GCT GGT N...N GCG GGT GGA G  GGG
                   CAACCTAGGGG CCT CGA CCA N...N CGC CCA CCT C  CCCTTAA
   mung bean nuclease treatment of the Eco R I site
                   GTTGGATCCCC GGA GCT GGT N...N GCG GGT GGA G  GGG
                   CAACCTAGGGG CCT CGA CCA N...N CGC CCA CCT C  CCC
   Bam H I digestion of pGEX-(GlyAla)n
                   GATC CCC GGA GCT GGT N...N GCG CGT GGA G  GGG
                        GGG CCT CGA CCA N...N CGC CCA CCT C  CCC iii. preparation of pGEM-9Zf:
   digestion of pGEM-9Zf with Xba I
   [SEQ ID NO: 44] N...TAGTAAGCTTTGCT         CTAGACTGGA...N
                   N...ATCATTCGAAACGAGATC     TGACCT...N
   mung bean treatment of the Xba I site
                   N...TAGTAAGCTTGCT           ACTGGA...N
                   N...ATCATTCGAAACGA          TCACCT...N
   Hind III digestion of pGEM-9Zf
                   N...TAGTA                   ACTGGAATTCGTCGACGAGTCCCTATACTN...N [SEQ ID NO: 46]
                   N...ATCATTCCA               TGACCTTAACCAGCTGCTCGAGGGATATCAN...N iv. tandem insertion of matrix and gly—ala into pGEM-9Zf:
   Hind III/Bam H I/blunt litigation:
                   PGEM-9ZI matrix PCR [SEQ ID NO: 42]              gly—ala
   [SEQ ID NO: 47] N.TA AGCTT ATG AGT N...N TTC AAG TG G ATC CCC   GGA GCT GGT N..N
                   N.ATTCGA A TAC TCA N...N AAG TTC ACC TAG GGG    CCT CGA CCA N..N
                   gly—ala   pGEM-8ZI                               stop
                   N...N GCG GGT GGA G GG G AC TCG AAT TCG TCG ACG AGC   TCC CTA TAG N..N
                   N...N CGC CCA CCT C CC C TG ACC TTA AGC AGC TGC TCG   AGG GAT ATC N..N
                            [SEQ ID 48]

I claim:

1. An amino acid sequence consisting of SEQ ID NO:1.

2. A fusion protein comprising the sequence of SEQ ID NO:1 and a core protein.

3. The fusion protein of claim 2, wherein said SEQ ID NO:1 is inserted within the amino acid sequence of said core protein.

4. The fusion protein of claim 2, wherein said SEQ ID NO:1 is joined to one of the carboxyl or amino terminus of said core protein.

5. The fusion protein of claim 2, wherein the first or last residue of said SEQID NO:1 is at a distance between about 1–300 residues from an epitope of said core protein.

6. The fusion protein of claim 2, wherein the the first or last residue of said SEQ ID NO:1 is at a distance between about 1–200 residues, from an epitope of said core protein.

7. The fusion protein of claim 6, wherein the distance between the site of insertion in the core protein of sequence of SEQ ID NO:1 and one amino acid of the core protein epitope is between about 20–50 residues, inclusive.

8. The fusion protein of claim 4, wherein the SEQ ID NO:1 is present within the fusion protein on the carboxy terminal side of an epitope of said core protein.

* * * * *

SEQUENCE LISTING ( 1 ) GENERAL INFORMATION:

( i i i ) NUMBER OF SEQUENCES: 76

( 2 ) INFORMATION FOR SEQ ID NO: 1:

( i ) SEQUENCE CHARACTERISTICS:
        ( A ) LENGTH: 235 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:1:

```
Gly Ala Gly Ala Gly Ala Gly Gly Ala Gly Ala Gly Gly Ala Gly Ala
  1               5                  10                  15
Gly Gly Gly Ala Gly Ala Gly Gly Gly Ala Gly Gly Ala Gly Gly Ala
             20                  25                  30
Gly Gly Ala Gly Ala Gly Gly Gly Ala Gly Ala Gly Gly Gly Ala Gly
         35                  40                  45
Gly Ala Gly Gly Ala Gly Ala Gly Gly Gly Ala Gly Ala Gly Gly Gly
     50                  55                  60
Ala Gly Gly Ala Gly Ala Gly Gly Gly Ala Gly Ala Gly Gly Gly Ala
 65                  70                  75                  80
Gly Ala Gly Gly Gly Ala Gly Ala Gly Gly Gly Ala Gly Gly Ala Gly
             85                  90                  95
Ala Gly Gly Gly Ala Gly Gly Ala Gly Gly Ala Gly Ala Gly Gly Gly
            100                 105                 110
Ala Gly Ala Gly Gly Ala Gly Gly Ala Gly Gly Ala Gly Ala Gly Gly
            115                 120                 125
Ala Gly Ala Gly Gly Gly Ala Gly Gly Ala Gly Gly Ala Gly Ala Gly
        130                 135                 140
Gly Ala Gly Ala Gly Gly Ala Gly Ala Gly Gly Ala Gly Ala Gly Gly
145                 150                 155                 160
Ala Gly Gly Ala Gly Ala Gly Gly Ala Gly Gly Ala Gly Ala Gly Gly
            165                 170                 175
Ala Gly Gly Ala Gly Ala Gly Gly Gly Ala Gly Gly Ala Gly Ala Gly
            180                 185                 190
Gly Gly Ala Gly Gly Ala Gly Ala Gly Gly Ala Gly Gly Ala Gly Ala
        195                 200                 205
Gly Gly Ala Gly Gly Ala Gly Ala Gly Gly Ala Gly Gly Ala Gly Ala
        210                 215                 220
Gly Gly Gly Ala Gly Ala Gly Gly Ala Gly Ala
225                 230                 235
```

( 2 ) INFORMATION FOR SEQ ID NO:2:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:2:

GGAGCTGGTG CTGGAGGTGC GGGT     24

( 2 ) INFORMATION FOR SEQ ID NO:3:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:3:

Gly Ala Gly Ala Gly Gly Ala Gly
1               5

( 2 ) INFORMATION FOR SEQ ID NO:4:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:4:

CTCCACCCGC ACCTCCAGCA CCAG                                              24

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:5:

GGAAGTGGAG CTGGAGGTGC GGGT                                              24

( 2 ) INFORMATION FOR SEQ ID NO:6:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( x i ) SEQUENCE DESCRIPTION: SEQ ID NO:6:

Gly Ser Gly Ala Gly Gly Ala Gly
1               5

( 2 ) INFORMATION FOR SEQ ID NO:7:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO: 7:

TTCCACCCGC ACCTCCAGCT CCAC                                              24

( 2 ) INFORMATION FOR SEQ ID NO:8:

( i ) SEQUENCE CHARACTERISTICS:
        ( A ) LENGTH: 24 bases (B) TYPE: nucleic acid
(C) STRANDEDNESS: single
(D) TOPOLOGY: linear (i i) MOLECULE TYPE: other nucleic acid (x i) SEQUENCE DESCRIPTION: SEQ ID NO:8:

GGAAGAGGAG CTGGAGGTGC GGGT 24

(2) INFORMATION FOR SEQ ID NO: 9:

(i) SEQUENCE CHARACTERISTICS:
(A) LENGTH: 8 amino acids
(B) TYPE: amino acid
(C) STRANDEDNESS: single
(D) TOPOLOGY: unknown (i i) MOLECULE TYPE: peptide (x i) SEQUENCE DESCRIPTION: SEQ ID NO:9:

Gly Arg Gly Ala Gly Gly Ala Gly
1               5

(2) INFORMATION FOR SEQ ID NO: 10:

(i) SEQUENCE CHARACTERISTICS:
(A) LENGTH: 24 bases
(B) TYPE: nucleic acid
(C) STRANDEDNESS: single
(D) TOPOLOGY: linear (x i) SEQUENCE DESCRIPTION: SEQ ID NO:10:

TTCCACCCGC ACCTCCAGCT CCTC 24

(2) INFORMATION FOR SEQ ID NO:11:

(i) SEQUENCE CHARACTERISTICS:
(A) LENGTH: 24 bases
(B) TYPE: nucleic acid
(C) STRANDEDNESS: single
(D) TOPOLOGY: linear (i i) MOLECULE TYPE: other nucleic acid (x i) SEQUENCE DESCRIPTION: SEQ ID NO:11:

GGAGAAGGAG CTGGAGGTGC GGGT 24

(2) INFORMATION FOR SEQ ID NO:12:

(i) SEQUENCE CHARACTERISTICS:
(A) LENGTH: 8 amino acids
(B) TYPE: amino acid
(C) STRANDEDNESS: single
(D) TOPOLOGY: unknown (i i) MOLECULE TYPE: peptide (x i) SEQUENCE DESCRIPTION: SEQ ID NO: 12:

Gly Glu Gly Ala Gly Gly Ala Gly
1               5

(2) INFORMATION FOR SEQ ID NO:13:

(i) SEQUENCE CHARACTERISTICS:
(A) LENGTH: 24 bases
(B) TYPE: nucleic acid
(C) STRANDEDNESS: single
(D) TOPOLOGY: linear (i i) MOLECULE TYPE: other nucleic acid ( x i ) SEQUENCE DESCRIPTION: SEQ ID NO:13:

CTCCACCCGC ACCTCCAGCT CCTT 24

( 2 ) INFORMATION FOR SEQ ID NO: 14:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO: 14:

GGATATGGAG CTGGAGGTGC GGGT 24

( 2 ) INFORMATION FOR SEQ ID NO: 15:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO: 15:

Gly Tyr Gly Ala Gly Gly Ala Gly
1               5

( 2 ) INFORMATION FOR SEQ ID NO: 16:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:16:

ATCCACCCGC ACCTCCAGCT CCAT 24

( 2 ) INFORMATION FOR SEQ ID NO:17:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:17:

GGATCAGGCA GCGGAGGTAG CGGT 24

( 2 ) INFORMATION FOR SEQ ID NO:18:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:18:

Gly Ser Gly Ser Gly Gly Ser Gly ( 2 ) INFORMATION FOR SEQ ID NO: 19:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO: 19:

ATCCACCGCT ACCTCCGCTG CCTG     24

( 2 ) INFORMATION FOR SEQ ID NO: 20:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:20:

GGACGTGGCC GAGGAGGTAG AGGT     24

( 2 ) INFORMATION FOR SEQ ID NO: 21:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO: 21:

Gly Arg Gly Arg Gly Gly Arg Gly
1             5

( 2 ) INFORMATION FOR SEQ ID NO:22:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:22:

GTCCACCTCT ACCTCCTCGG CCAC     24

( 2 ) INFORMATION FOR SEQ ID NO:23:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:23:

GGAGAGGGCG AAGGAGGTGA AGGT     24

( 2 ) INFORMATION FOR SEQ ID NO:24:

(i) SEQUENCE CHARACTERISTICS:
  (A) LENGTH: 8 amino acids
  (B) TYPE: amino acid
  (C) STRANDEDNESS: single
  (D) TOPOLOGY: unknown (ii) MOLECULE TYPE: peptide (xi) SEQUENCE DESCRIPTION: SEQ ID NO:24:

Gly Glu Gly Glu Gly Gly Glu Gly
1               5

(2) INFORMATION FOR SEQ ID NO: 25:

(i) SEQUENCE CHARACTERISTICS:
  (A) LENGTH: 24 base pairs
  (B) TYPE: nucleic acid
  (C) STRANDEDNESS: single
  (D) TOPOLOGY: linear (ii) MOLECULE TYPE: other nucleic acid (xi) SEQUENCE DESCRIPTION: SEQ ID NO: 25:

CTCCACCTTC ACCTCCTTCG CCCT  24

(2) INFORMATION FOR SEQ ID NO: 26:

(i) SEQUENCE CHARACTERISTICS:
  (A) LENGTH: 24 base pairs
  (B) TYPE: nucleic acid
  (C) STRANDEDNESS: double
  (D) TOPOLOGY: linear (ii) MOLECULE TYPE: other nucleic acid (xi) SEQUENCE DESCRIPTION: SEQ ID NO:26:

GTTGGATCCC CGGGAATTCA TCGT  24

(2) INFORMATION FOR SEQ ID NO:27:

(i) SEQUENCE CHARACTERISTICS:
  (A) LENGTH: 10 base pairs
  (B) TYPE: nucleic acid
  (C) STRANDEDNESS: double
  (D) TOPOLOGY: linear (ii) MOLECULE TYPE: other nucleic acid (xi) SEQUENCE DESCRIPTION: SEQ ID NO:27:

GGAGCTGGTN  10

(2) INFORMATION FOR SEQ ID NO:28:

(i) SEQUENCE CHARACTERISTICS:
  (A) LENGTH: 21 base pairs
  (B) TYPE: nucleic acid
  (C) STRANDEDNESS: double
  (D) TOPOLOGY: linear (ii) MOLECULE TYPE: other nucleic acid (xi) SEQUENCE DESCRIPTION: SEQ ID NO:28:

GTTGGATCCC CGGAGCTGGT N  21

(2) INFORMATION FOR SEQ ID NO:29:

(i) SEQUENCE CHARACTERISTICS:
  (A) LENGTH: 15 base pairs
  (B) TYPE: nucleic acid ( C ) STRANDEDNESS: double
( D ) TOPOLOGY: linear ( i i ) MOLECULE TYPE: other nucleic acid ( x i ) SEQUENCE DESCRIPTION: SEQ ID NO:29:

GAAACGTACG TTCTC 15

( 2 ) INFORMATION FOR SEQ ID NO: 30:

( i ) SEQUENCE CHARACTERISTICS:
( A ) LENGTH: 11 base pairs
( B ) TYPE: nucleic acid
( C ) STRANDEDNESS: double
( D ) TOPOLOGY: linear ( i i ) MOLECULE TYPE: other nucleic acid ( x i ) SEQUENCE DESCRIPTION: SEQ ID NO: 30:

NGCGGGTGGA G 11

( 2 ) INFORMATION FOR SEQ ID NO:31:

( i ) SEQUENCE CHARACTERISTICS:
( A ) LENGTH: 24 base pairs
( B ) TYPE: nucleic acid
( C ) STRANDEDNESS: double
( D ) TOPOLOGY: linear ( i i ) MOLECULE TYPE: other nucleic acid ( x i ) SEQUENCE DESCRIPTION: SEQ ID NO:31:

NGCGGGTGGA GGGGAATTCA TCGT 24

( 2 ) INFORMATION FOR SEQ ID NO: 32:

( i ) SEQUENCE CHARACTERISTICS:
( A ) LENGTH: 22 base pairs
( B ) TYPE: nucleic acid
( C ) STRANDEDNESS: double
( D ) TOPOLOGY: linear ( i i ) MOLECULE TYPE: other nucleic acid ( x i ) SEQUENCE DESCRIPTION: SEQ ID NO: 32:

NGCGGGTGGA GGGGACGTTC TC 22

( 2 ) INFORMATION FOR SEQ ID NO: 33:

( i ) SEQUENCE CHARACTERISTICS:
( A ) LENGTH: 22 base pairs
( B ) TYPE: nucleic acid
( C ) STRANDEDNESS: double
( D ) TOPOLOGY: linear ( i i ) MOLECULE TYPE: other nucleic acid ( x i ) SEQUENCE DESCRIPTION: SEQ ID NO: 33:

GAAACGTTCC CCGGAGCTGG TN 22

( 2 ) INFORMATION FOR SEQ ID NO: 34:

( i ) SEQUENCE CHARACTERISTICS:
( A ) LENGTH: 18 base pairs
( B ) TYPE: nucleic acid
( C ) STRANDEDNESS: double
( D ) TOPOLOGY: linear ( i i ) MOLECULE TYPE: genomic DNA ( x i ) SEQUENCE DESCRIPTION: SEQ ID NO: 34:

AACGGGGATC CAAATAAC 18

( 2 ) INFORMATION FOR SEQ ID NO: 35:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: other nucleic acid ( x i ) SEQUENCE DESCRIPTION: SEQ ID NO: 35:

NGCGGGTGGA GGGGAAGATC CA 22

( 2 ) INFORMATION FOR SEQ ID NO: 36:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: other nucleic acid ( x i ) SEQUENCE DESCRIPTION: SEQ ID NO: 36:

NGCGGGTGGA GGGGCCTATC AG 22

( 2 ) INFORMATION FOR SEQ ID NO: 37:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: genomic DNA ( x i ) SEQUENCE DESCRIPTION: SEQ ID NO: 37:

NTTCAAGTGG ATCCTCG 17

( 2 ) INFORMATION FOR SEQ ID NO: 38:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: other nucleic acid ( x i ) SEQUENCE DESCRIPTION: SEQ ID NO: 38:

GGGGATCTCC CCGGAGCTGG TN 22

( 2 ) INFORMATION FOR SEQ ID NO:39:

( i ) SEQUENCE CHARACTERISTICS:
        ( A ) LENGTH: 15 base pairs
        ( B ) TYPE: nucleic acid
        ( C ) STRANDEDNESS: double
        ( D ) TOPOLOGY: linear ( i i ) MOLECULE TYPE: other nucleic acid ( x i ) SEQUENCE DESCRIPTION: SEQ ID NO:39:

TTGCAGGCCT ATCAG 15

( 2 ) INFORMATION FOR SEQ ID NO:40:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: other nucleic acid ( x i ) SEQUENCE DESCRIPTION: SEQ ID NO:40:

TTGCAGGTCC CCGGAGCTGG TN        22

( 2 ) INFORMATION FOR SEQ ID NO:41:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: other nucleic acid ( x i ) SEQUENCE DESCRIPTION: SEQ ID NO:41:

ATAAAGCTTA TGAGTN        16

( 2 ) INFORMATION FOR SEQ ID NO:42:

( i ) SEQUENCE CHARACTERISTICS:
        ( A ) LENGTH: 26 base pairs
        ( B ) TYPE: nucleic acid
        ( C ) STRANDEDNESS: double
        ( D ) TOPOLOGY: linear ( i i ) MOLECULE TYPE: other nucleic acid ( x i ) SEQUENCE DESCRIPTION: SEQ ID NO: 42:

NTTCAAGTGG ATCCCCGGAG CTGGTN        2

( 2 ) INFORMATION FOR SEQ ID NO: 43:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO: 43:

Gly Ile Leu Gly Phe Val Phe Thr Leu
1                5

( 2 ) INFORMATION FOR SEQ ID NO: 44:

( i ) SEQUENCE CHARACTERISTICS:
        ( A ) LENGTH: 24 base pairs
        ( B ) TYPE: nucleic acid
        ( C ) STRANDEDNESS: double
        ( D ) TOPOLOGY: linear ( i i ) MOLECULE TYPE: other nucleic acid ( x i ) SEQUENCE DESCRIPTION: SEQ ID NO: 44:

TAGTAAGCTT TGCTCTAGAC TGGA        24

( 2 ) INFORMATION FOR SEQ ID NO: 45:

( i ) SEQUENCE CHARACTERISTICS:
        ( A ) LENGTH: 8 amino acids ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO: 45:

```
Val His Leu Tyr Leu Leu Gly His
1               5
```

( 2 ) INFORMATION FOR SEQ ID NO: 46:

( i ) SEQUENCE CHARACTERISTICS:
            ( A ) LENGTH: 31 base pairs
            ( B ) TYPE: nucleic acid
            ( C ) STRANDEDNESS: double
            ( D ) TOPOLOGY: linear ( i i ) MOLECULE TYPE: other nucleic acid ( x i ) SEQUENCE DESCRIPTION: SEQ ID NO: 46:

```
ACTGGAATTC GTCGACGAGC TCCCTATAGT N                                          31
```

( 2 ) INFORMATION FOR SEQ ID NO: 47:

( i ) SEQUENCE CHARACTERISTICS:
            ( A ) LENGTH: 14 base pairs
            ( B ) TYPE: nucleic acid
            ( C ) STRANDEDNESS: double
            ( D ) TOPOLOGY: linear ( i i ) MOLECULE TYPE: other nucleic acid ( x i ) SEQUENCE DESCRIPTION: SEQ ID NO: 47:

```
TAAGCTTATG AGTN                                                             14
```

( 2 ) INFORMATION FOR SEQ ID NO: 48:

( i ) SEQUENCE CHARACTERISTICS:
            ( A ) LENGTH: 44 base pairs
            ( B ) TYPE: nucleic acid
            ( C ) STRANDEDNESS: double
            ( D ) TOPOLOGY: linear ( i i ) MOLECULE TYPE: other nucleic acid ( x i ) SEQUENCE DESCRIPTION: SEQ ID NO: 48:

```
NGCGGGTGGA GGGGACTGGA ATTCGTCGAC GAGCTCCCTA TAGN                             44
```

( 2 ) INFORMATION FOR SEQ ID NO: 49:

( i ) SEQUENCE CHARACTERISTICS:
            ( A ) LENGTH: 12 amino acids
            ( B ) TYPE: amino acid
            ( C ) STRANDEDNESS: single
            ( D ) TOPOLOGY: unknown ( i i ) MOLECULE TYPE: peptide ( i i i ) HYPOTHETICAL: yes ( i x ) FEATURE:
            ( A ) NAME/KEY: Region
            ( B ) LOCATION: 2
            ( C ) OTHER INFORMATION: Gly at position 2 may be present or
                    absent ( i x ) FEATURE:
            ( A ) NAME/KEY: Region
            ( B ) LOCATION: 3
            ( C ) OTHER INFORMATION: Gly at position 3 may be present or
                    absent ( i x ) FEATURE:
    ( A ) NAME/KEY: Region
    ( B ) LOCATION: 4
    ( C ) OTHER INFORMATION: Xaa at position 4 is a hydrophobic or polar amino acid without a ring structure and having a side-chain of less than 3 atoms ( i x ) FEATURE:
    ( A ) NAME/KEY: Region
    ( B ) LOCATION: 6
    ( C ) OTHER INFORMATION: Gly at position 6 may be present or absent ( i x ) FEATURE:
    ( A ) NAME/KEY: Region
    ( B ) LOCATION: 7
    ( C ) OTHER INFORMATION: Gly at position 7 may be present or absent ( i x ) FEATURE:
    ( A ) NAME/KEY: Region
    ( B ) LOCATION: 8
    ( C ) OTHER INFORMATION: Xaa at position 8 is a hydrophobic or polar amino acid without a ring structure and having a side-chain of less than 3 atoms ( i x ) FEATURE:
    ( A ) NAME/KEY: Region
    ( B ) LOCATION: 10
    ( C ) OTHER INFORMATION: Gly at position 10 may be present or absent ( i x ) FEATURE:
    ( A ) NAME/KEY: Region
    ( B ) LOCATION: 11
    ( C ) OTHER INFORMATION: Gly at position 11 may be present or absent ( i x ) FEATURE:
    ( A ) NAME/KEY: Region
    ( B ) LOCATION: 12
    ( C ) OTHER INFORMATION: Xaa at position 12 is a hydrophobic or polar amino acid without a ring structure and having a side-chain of less than 3 atoms ( x i ) SEQUENCE DESCRIPTION: SEQ ID NO:49:

Gly Gly Gly Xaa Gly Gly Gly Xaa Gly Gly Gly Xaa
1                5                        10

( 2 ) INFORMATION FOR SEQ ID NO: 50:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: yes ( i x ) FEATURE:
        ( A ) NAME/KEY: Region
        ( B ) LOCATION: 3
        ( C ) OTHER INFORMATION: Xaa at position 3 is a hydrophobic or polar amino acid without a ring structure and having a side-chain of less than 3 atoms ( i x ) FEATURE:
        ( A ) NAME/KEY: Region
        ( B ) LOCATION: 5
        ( C ) OTHER INFORMATION: Xaa at position 5 is a hydrophobic or polar amino acid without a ring structure and having a side-chain of less than 3 atoms ( i x ) FEATURE:
        ( A ) NAME/KEY: Region (B) LOCATION: 7
(C) OTHER INFORMATION: Xaa at position 7 is a hydrophobic or polar amino acid without a ring structure and having a side-chain of less than 3 atoms (xi) SEQUENCE DESCRIPTION: SEQ ID NO: 50:

Gly Gly Xaa Gly Xaa Gly Xaa
1               5

(2) INFORMATION FOR SEQ ID NO: 51:

(i) SEQUENCE CHARACTERISTICS:
(A) LENGTH: 8 amino acids
(B) TYPE: amino acid
(C) STRANDEDNESS: single
(D) TOPOLOGY: unknown (ii) MOLECULE TYPE: peptide (iii) HYPOTHETICAL: yes (ix) FEATURE:
(A) NAME/KEY: Region
(B) LOCATION: 3
(C) OTHER INFORMATION: Xaa at position 3 is a hydrophobic or polar amino acid without a ring structure and having a side-chain of less than 3 atoms (ix) FEATURE:
(A) NAME/KEY: Region
(B) LOCATION: 5
(C) OTHER INFORMATION: Xaa at position 5 is a hydrophobic or polar amino acid without a ring structure and having a side-chain of less than 3 atoms (ix) FEATURE:
(A) NAME/KEY: Region
(B) LOCATION: 8
(C) OTHER INFORMATION: Xaa at position 8 is a hydrophobic or polar amino acid without a ring structure and having a side-chain of less than 3 atoms (xi) SEQUENCE DESCRIPTION: SEQ ID NO: 51:

Gly Gly Xaa Gly Xaa Gly Gly Xaa
1               5

(2) INFORMATION FOR SEQ ID NO: 52:

(i) SEQUENCE CHARACTERISTICS:
(A) LENGTH: 9 amino acids
(B) TYPE: amino acid
(C) STRANDEDNESS: single
(D) TOPOLOGY: unknown (ii) MOLECULE TYPE: peptide (iii) HYPOTHETICAL: yes (ix) FEATURE:
(A) NAME/KEY: Region
(B) LOCATION: 3
(C) OTHER INFORMATION: Xaa at position 3 is a hydrophobic or polar amino acid without a ring structure and having a side-chain of less than 3 atoms (ix) FEATURE:
(A) NAME/KEY: Region
(B) LOCATION: 5
(C) OTHER INFORMATION: Xaa at position 5 is a hydrophobic or polar amino acid without a ring structure and having a side-chain of less than 3 atoms (ix) FEATURE:
(A) NAME/KEY: Region
(B) LOCATION: 9
(C) OTHER INFORMATION: Xaa at position 9 is a hydrophobic or polar amino acid without a ring structure and having a
side-chain of less than 3 atoms ( x i ) SEQUENCE DESCRIPTION: SEQ ID NO:52:

Gly Gly Xaa Gly Xaa Gly Gly Gly Xaa
1               5

( 2 ) INFORMATION FOR SEQ ID NO: 53:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 53:

Gly Gly Ala Gly Ala Gly Gly Ala
1               5

( 2 ) INFORMATION FOR SEQ ID NO: 54:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO: 54:

Gly Gly Ala Gly Ala Gly Gly Gly Ala
1               5

( 2 ) INFORMATION FOR SEQ ID NO: 55:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 55:

Gly Gly Ser Gly Ala Gly Ala
1               5

( 2 ) INFORMATION FOR SEQ ID NO:56:

( i ) SEQUENCE CHARACTERISTICS:
        ( A ) LENGTH: 26 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:56:

TGAATTCTCG ACCCCGGCCT CCACTG    26

( 2 ) INFORMATION FOR SEQ ID NO: 57:

( i ) SEQUENCE CHARACTERISTICS:
        ( A ) LENGTH: 32 bases
        ( B ) TYPE: nucleic acid
        ( C ) STRANDEDNESS: single
        ( D ) TOPOLOGY: linear -continued ( i i ) MOLECULE TYPE: other nucleic acid ( x i ) SEQUENCE DESCRIPTION: SEQ ID NO: 57:

CATGCCATAG TAACTGACTT TAGTGTAATC AA                32

( 2 ) INFORMATION FOR SEQ ID NO: 58:

( i ) SEQUENCE CHARACTERISTICS:
        ( A ) LENGTH: 31 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO: 58:

CATGCTTGAT TACACTTAAG TCAGTTACTA T                 31

( 2 ) INFORMATION FOR SEQ ID NO: 59:

( i ) SEQUENCE CHARACTERISTICS:
        ( A ) LENGTH: 29 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO: 59:

CGATCGTAAC TGACTTTAGT GTAATCAGG                    29

( 2 ) INFORMATION FOR SEQ ID NO: 60:

( i ) SEQUENCE CHARACTERISTICS:
        ( A ) LENGTH: 33 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO: 60:

CCTTGATTAC ACTAAAGTCA GTTACGATCG TGC               33

( 2 ) INFORMATION FOR SEQ ID NO: 61:

( i ) SEQUENCE CHARACTERISTICS:
        ( A ) LENGTH: 33 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO: 61:

TAACGATCGT AACTGACTTT AGTGTAATCA AGG               33

( 2 ) INFORMATION FOR SEQ ID NO: 62:

( i ) SEQUENCE CHARACTERISTICS:
        ( A ) LENGTH: 32 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO: 62:

TTACCTTGAT TACACTAAGT CAGTTACGAT CG                32

(2) INFORMATION FOR SEQ ID NO: 63:

(i) SEQUENCE CHARACTERISTICS:
(A) LENGTH: 26 bases
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO: 63:

AAGGATCCAA GTTGCATTGG ATGCAA 26

(2) INFORMATION FOR SEQ ID NO: 64:

(i) SEQUENCE CHARACTERISTICS:
(A) LENGTH: 8 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO: 64:

Leu His Leu His Leu Leu Arg Pro
1               5

(2) INFORMATION FOR SEQ ID NO: 65:

(i) SEQUENCE CHARACTERISTICS:
(A) LENGTH: 30 bases
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO: 65:

ATAAAGCTTA TGAGTCTTCT AACCGAGGTC 30

(2) INFORMATION FOR SEQ ID NO: 66:

(i) SEQUENCE CHARACTERISTICS:
(A) LENGTH: 29 bases
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO: 66:

CGAGGATCCA CTTGAACCGT TGCATCTGC 29

(2) INFORMATION FOR SEQ ID NO: 67:

(i) SEQUENCE CHARACTERISTICS:
(A) LENGTH: 9 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO: 67:

Ile Val Thr Asp Phe Ser Val Ile Lys
1               5

(2) INFORMATION FOR SEQ ID NO: 68:

( i ) SEQUENCE CHARACTERISTICS:
   ( A ) LENGTH: 8 amino acids
   ( B ) TYPE: amino acid
   ( C ) STRANDEDNESS: single
   ( D ) TOPOLOGY: unknown ( i i ) MOLECULE TYPE: peptide ( x i ) SEQUENCE DESCRIPTION: SEQ ID NO: 68:

Leu His Pro His Leu Gln His Gln
1               5

( 2 ) INFORMATION FOR SEQ ID NO: 69:

( i ) SEQUENCE CHARACTERISTICS:
   ( A ) LENGTH: 8 amino acids
   ( B ) TYPE: amino acid
   ( C ) STRANDEDNESS: single
   ( D ) TOPOLOGY: unknown ( i i ) MOLECULE TYPE: peptide ( x i ) SEQUENCE DESCRIPTION: SEQ ID NO: 69:

Phe His Pro His Leu Gln Leu His
1               5

( 2 ) INFORMATION FOR SEQ ID NO: 70:

( i ) SEQUENCE CHARACTERISTICS:
   ( A ) LENGTH: 8 amino acids
   ( B ) TYPE: amino acid
   ( C ) STRANDEDNESS: single
   ( D ) TOPOLOGY: unknown ( i i ) MOLECULE TYPE: peptide ( x i ) SEQUENCE DESCRIPTION: SEQ ID NO: 70:

Phe His Pro His Leu Gln Leu Leu
1               5

( 2 ) INFORMATION FOR SEQ ID NO: 71:

( i ) SEQUENCE CHARACTERISTICS:
   ( A ) LENGTH: 8 amino acids
   ( B ) TYPE: amino acid
   ( C ) STRANDEDNESS: single
   ( D ) TOPOLOGY: unknown ( i i ) MOLECULE TYPE: peptide ( x i ) SEQUENCE DESCRIPTION: SEQ ID NO: 71:

Leu His Pro His Leu Gln Leu Leu
1               5

( 2 ) INFORMATION FOR SEQ ID NO: 72:

( i ) SEQUENCE CHARACTERISTICS:
   ( A ) LENGTH: 8 amino acids
   ( B ) TYPE: amino acid
   ( C ) STRANDEDNESS: single
   ( D ) TOPOLOGY: unknown ( i i ) MOLECULE TYPE: peptide ( x i ) SEQUENCE DESCRIPTION: SEQ ID NO: 72:

Ile His Pro His Leu Gln Leu His
1               5

( 2 ) INFORMATION FOR SEQ ID NO: 73:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO: 73:

```
Ile His Arg Tyr Leu Arg Cys Leu
1               5
```

( 2 ) INFORMATION FOR SEQ ID NO: 74:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: unknown ( i i ) MOLECULE TYPE: peptide ( i x ) FEATURE:
        ( A ) NAME/KEY: region
        ( B ) LOCATION: 4
        ( C ) OTHER INFORMATION: Gly at position 4 may be present or absent ( i x ) FEATURE:
        ( A ) NAME/KEY: region
        ( B ) LOCATION: 5
        ( C ) OTHER INFORMATION: Gly at position 5 may be present or absent ( i x ) FEATURE:
        ( A ) NAME/KEY: region
        ( B ) LOCATION: 6
        ( C ) OTHER INFORMATION: Xaa at position 6 is a hydrophobic or polar amino acid without a ring structure and having a side-chain of less than 3 atoms ( i x ) FEATURE:
        ( A ) NAME/KEY: region
        ( B ) LOCATION: 8
        ( C ) OTHER INFORMATION: Gly at position 8 may be present or absent ( i x ) FEATURE:
        ( A ) NAME/KEY: region
        ( B ) LOCATION: 9
        ( C ) OTHER INFORMATION: Gly at position 9 may be present or absent ( i x ) FEATURE:
        ( A ) NAME/KEY: region
        ( B ) LOCATION: 10
        ( C ) OTHER INFORMATION: Xaa at position 10 is a hydrophobic or polar amino acid without a ring structure and having a side-chain of less than 3 atoms ( i x ) FEATURE:
        ( A ) NAME/KEY: region
        ( B ) LOCATION: 12
        ( C ) OTHER INFORMATION: Gly at position 12 may be present or absent ( i x ) FEATURE:
        ( A ) NAME/KEY: region
        ( B ) LOCATION: 13
        ( C ) OTHER INFORMATION: Gly at position 13 may be present or absent ( i x ) FEATURE:
        ( A ) NAME/KEY: region
        ( B ) LOCATION: 14
        ( C ) OTHER INFORMATION: Xaa at position 14 is a hydrophobic or polar amino acid without a ring structure and having a side-chain of less than 3 atoms ( i x ) FEATURE:
    ( A ) NAME/KEY: region
    ( B ) LOCATION: 3-14
    ( C ) OTHER INFORMATION: The sequence encompassed by amino
          acids 3-14 may be present in one copy or in two or more
          tandemly- arranged copies placed after the Pro at position
          2 and before the Asp at position 15

( x i ) SEQUENCE DESCRIPTION: SEQ ID NO: 74:

```
Phe  Pro  Gly  Gly  Gly  Xaa  Gly  Gly  Gly  Xaa  Gly  Gly  Gly  Xaa  Asp
1              5                        10                       15
```

( 2 ) INFORMATION FOR SEQ ID NO: 75:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: unknown ( i i ) MOLECULE TYPE: peptide ( i x ) FEATURE:
        ( A ) NAME/KEY: region
        ( B ) LOCATION: 4
        ( C ) OTHER INFORMATION: Gly at position 4 may be present or
            absent ( i x ) FEATURE:
        ( A ) NAME/KEY: region
        ( B ) LOCATION: 5
        ( C ) OTHER INFORMATION: Gly at position 5 may be present or
            absent ( i x ) FEATURE:
        ( A ) NAME/KEY: region
        ( B ) LOCATION: 6
        ( C ) OTHER INFORMATION: Xaa at position 6 is a hydrophobic or
            polar amino acid without a ring structure and having a
            side-chain of less than 3 atoms ( i x ) FEATURE:
        ( A ) NAME/KEY: region
        ( B ) LOCATION: 8
        ( C ) OTHER INFORMATION: Gly at position 8 may be present or
            absent ( i x ) FEATURE:
        ( A ) NAME/KEY: region
        ( B ) LOCATION: 9
        ( C ) OTHER INFORMATION: Gly at position 9 may be present or
            absent ( i x ) FEATURE:
        ( A ) NAME/KEY: region
        ( B ) LOCATION: 10
        ( C ) OTHER INFORMATION: Xaa at position 10 is a hydrophobic
            or polar amino acid without a ring structure and having a
            side-chain of less than 3 atoms ( i x ) FEATURE:
        ( A ) NAME/KEY: region
        ( B ) LOCATION: 12
        ( C ) OTHER INFORMATION: Gly at position 12 may be present or
            absent ( i x ) FEATURE:
        ( A ) NAME/KEY: region
        ( B ) LOCATION: 13
        ( C ) OTHER INFORMATION: Gly at position 13 may be present or
            absent ( i x ) FEATURE:
        ( A ) NAME/KEY: region
        ( B ) LOCATION: 14
        ( C ) OTHER INFORMATION: Xaa at position 14 is a hydrophobic or polar amino acid without a ring structure and having a side-chain of less than 3 atoms (ix) FEATURE:
 (A) NAME/KEY: region
 (B) LOCATION: 3-14
 (C) OTHER INFORMATION: The sequence encompassed by amino acids 3-14 may be present in one copy or in two or more tandemly- arranged copies placed after the Pro at position 2 and before the Glu at position 15

(xi) SEQUENCE DESCRIPTION: SEQ ID NO: 75:

```
Leu  Pro  Gly  Gly  Gly  Xaa  Gly  Gly  Gly  Xaa  Gly  Gly  Gly  Xaa  Glu
1                  5                        10                       15
```

(2) INFORMATION FOR SEQ ID NO: 76:

(i) SEQUENCE CHARACTERISTICS:
  (A) LENGTH: 14 amino acids
  (B) TYPE: amino acid
  (C) STRANDEDNESS: single
  (D) TOPOLOGY: unknown (ii) MOLECULE TYPE: peptide (ix) FEATURE:
  (A) NAME/KEY: region
  (B) LOCATION: 4
  (C) OTHER INFORMATION: Gly at position 4 may be present or absent (ix) FEATURE:
  (A) NAME/KEY: region
  (B) LOCATION: 5
  (C) OTHER INFORMATION: Gly at position 5 may be present or absent (ix) FEATURE:
  (A) NAME/KEY: region
  (B) LOCATION: 6
  (C) OTHER INFORMATION: Xaa at position 6 is a hydrophobic or polar amino acid without a ring structure and having a side-chain of less than 3 atoms (ix) FEATURE:
  (A) NAME/KEY: region
  (B) LOCATION: 8
  (C) OTHER INFORMATION: Gly at position 8 may be present or absent (ix) FEATURE:
  (A) NAME/KEY: region
  (B) LOCATION: 9
  (C) OTHER INFORMATION: Gly at position 9 may be present or absent (ix) FEATURE:
  (A) NAME/KEY: region
  (B) LOCATION: 10
  (C) OTHER INFORMATION: Xaa at position 10 is a hydrophobic or polar amino acid without a ring structure and having a side-chain of less than 3 atoms (ix) FEATURE:
  (A) NAME/KEY: region
  (B) LOCATION: 12
  (C) OTHER INFORMATION: Gly at position 12 may be present or absent (ix) FEATURE:
  (A) NAME/KEY: region
  (B) LOCATION: 13
  (C) OTHER INFORMATION: Gly at position 13 may be present or absent (ix) FEATURE:
  (A) NAME/KEY: region
  (B) LOCATION: 14

-continued ( C ) OTHER INFORMATION: Xaa at position 14 is a hydrophobic or polar amino acid without a ring structure and having a side-chain of less than 3 atoms ( i x ) FEATURE:
( A ) NAME/KEY: region
( B ) LOCATION: 3-14
( C ) OTHER INFORMATION: The sequence encompassed by amino acids 3-14 may be present in one copy or in two or more tandemly- arranged copies placed after the Pro at position 2

( x i ) SEQUENCE DESCRIPTION: SEQ ID NO: 76:

Val Pro Gly Gly Gly Xaa Gly Gly Gly Xaa Gly Gly Gly Xaa
1 5 10